(12) United States Patent
Cornhill et al.

(10) Patent No.: US 10,874,286 B2
(45) Date of Patent: *Dec. 29, 2020

(54) METHOD AND APPARATUS FOR MANIPULATING THE SIDE WALL OF A BODY LUMEN OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME

(71) Applicant: Cornell University, New York, NY (US)

(72) Inventors: John Frederick Cornhill, New York, NY (US); Jeffery Milsom, New York, NY (US); Sameer Sharma, New York, NY (US); Tuan Anh Nguyen, Woburn, MA (US); Christopher Dillon, Underhill, VT (US); Gabriel Greeley, Cambridge, MA (US); Rahul Sathe, Somerville, MA (US); Matthew DeNardo, Melrose, MA (US); Ashley Whitney, Somerville, MA (US); Jeremy Van Hill, Somerville, MA (US); Anthony Assal, Bronx, NY (US)

(73) Assignee: Cornell University, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/000,104

(22) Filed: Jun. 5, 2018

(65) Prior Publication Data

US 2019/0133420 A1   May 9, 2019

Related U.S. Application Data

(63) Continuation of application No. 14/619,845, filed on Feb. 11, 2015, now Pat. No. 9,986,893, which is a
(Continued)

(51) Int. Cl.
*A61B 1/00* (2006.01)
*A61M 25/10* (2013.01)
(Continued)

(52) U.S. Cl.
CPC ...... *A61B 1/00082* (2013.01); *A61B 1/00135* (2013.01); *A61B 1/00154* (2013.01);
(Continued)

(58) Field of Classification Search
CPC .......... A61M 25/1011; A61M 25/1018; A61M 2025/1015; A61M 2025/1013;
(Continued)

(56) References Cited

U.S. PATENT DOCUMENTS

| 2,473,742 A | 6/1949 | Auzin |
| 4,066,071 A | 1/1978 | Nagel |

(Continued)

FOREIGN PATENT DOCUMENTS

| AU | 2012 203 616 A1 | 7/2012 |
| CA | 2988249 | 12/2016 |

(Continued)

*Primary Examiner* — Katrina M Stransky
(74) *Attorney, Agent, or Firm* — Pandiscio & Pandiscio

(57) ABSTRACT

Apparatus comprising: a sleeve adapted to be slid over the exterior of an endoscope; a proximal balloon secured to the sleeve; an inflation/deflation tube carried by the sleeve and in fluid communication with the interior of the proximal balloon; a push tube slidably mounted to the sleeve; and a distal balloon secured to the distal end of the push tube, the interior of the distal balloon being in fluid communication with the push tube, wherein the distal balloon is capable of assuming a deflated condition and an inflated condition, and further wherein when the distal balloon is in its deflated condition, an axial opening extends therethrough, the axial
(Continued)

opening being sized to receive the endoscope therein, and when the distal balloon is in its inflated condition, the axial opening is closed down.

13 Claims, 36 Drawing Sheets

Related U.S. Application Data continuation-in-part of application No. 14/540,355, filed on Nov. 13, 2014, now Pat. No. 9,924,853, which is a continuation of application No. 12/969,059, filed on Dec. 15, 2010, now Pat. No. 8,979,884.

(60) Provisional application No. 61/284,215, filed on Dec. 15, 2009, provisional application No. 61/938,446, filed on Feb. 11, 2014.

(51) Int. Cl.
*A61B 1/31* (2006.01)
*A61M 25/00* (2006.01)

(52) U.S. Cl.
CPC ........... *A61B 1/31* (2013.01); *A61M 25/1011* (2013.01); *A61M 25/1018* (2013.01); *A61M 25/10182* (2013.11); *A61M 25/10187* (2013.11); *A61M 2025/0008* (2013.01); *A61M 2025/1015* (2013.01)

(58) Field of Classification Search
CPC ....... A61M 2025/1052; A61B 1/00135; A61B 1/00154; A61B 1/31; A61B 1/00082; A61B 17/12045; A61B 17/1204; A61B 17/12136
See application file for complete search history.

(56) References Cited

U.S. PATENT DOCUMENTS

| | | | |
|---|---|---|---|
| 4,198,981 A | 4/1980 | Sinnreich | |
| 4,224,929 A | 9/1980 | Furihata | |
| 4,445,892 A | 5/1984 | Hussein et al. | |
| 4,862,874 A | 9/1989 | Kellner | |
| 5,025,778 A | 6/1991 | Silverstein et al. | |
| 5,078,731 A | 1/1992 | Hayhurst | |
| 5,105,800 A | 4/1992 | Takahashi et al. | |
| 5,147,382 A | 9/1992 | Gertzman et al. | |
| 5,197,971 A | 3/1993 | Bonutti | |
| 5,217,001 A * | 6/1993 | Nakao | A61B 1/00135 24/DIG. 50 |
| 5,423,821 A | 6/1995 | Pasque | |
| 5,662,587 A | 9/1997 | Grundfest et al. | |
| 5,718,680 A | 2/1998 | Kraus et al. | |
| 5,762,604 A | 6/1998 | Kieturakis | |
| 5,833,650 A | 11/1998 | Imran | |
| 5,938,585 A | 8/1999 | Donofrio | |
| 5,954,731 A | 9/1999 | Yoon | |
| 6,007,482 A | 12/1999 | Madni et al. | |
| 6,007,483 A | 12/1999 | Kieturakis | |
| 6,071,273 A | 6/2000 | Euteneuer et al. | |
| 6,139,517 A | 10/2000 | Macoviak et al. | |
| 6,234,958 B1 | 5/2001 | Snoke et al. | |
| 6,277,065 B1 | 8/2001 | Donofrio | |
| 6,309,346 B1 | 10/2001 | Farhadi | |
| 6,375,665 B1 | 4/2002 | Nash et al. | |
| 6,475,226 B1 | 11/2002 | Belef et al. | |
| 6,575,932 B1 | 6/2003 | O'Brien et al. | |
| 6,585,639 B1 | 7/2003 | Kotmel et al. | |
| 6,741,884 B1 | 5/2004 | Freeman et al. | |
| 6,764,441 B2 | 7/2004 | Chiel et al. | |
| 6,790,173 B2 | 9/2004 | Saadat et al. | |
| 6,793,661 B2 | 9/2004 | Hamilton et al. | |
| 6,929,601 B2 | 8/2005 | Nakao | |
| 6,951,554 B2 | 10/2005 | Johansen et al. | |
| 6,988,986 B2 | 1/2006 | Gross | |
| 7,041,051 B2 | 5/2006 | Bernstein | |
| 7,410,483 B2 | 8/2008 | Danitz et al. | |
| 7,510,523 B2 | 3/2009 | Sakamoto | |
| 7,591,782 B2 | 9/2009 | Fujikura | |
| 7,635,346 B2 | 12/2009 | Cabiri et al. | |
| 7,678,044 B2 | 3/2010 | Fujikura | |
| 7,699,771 B2 | 4/2010 | Wendlandt | |
| 7,708,687 B2 | 5/2010 | Bern et al. | |
| 7,798,992 B2 | 9/2010 | Ortiz | |
| 7,833,150 B2 | 11/2010 | Yamamoto et al. | |
| 7,901,347 B2 | 3/2011 | Sekiguchi et al. | |
| 7,909,755 B2 | 3/2011 | Itoi | |
| 7,935,047 B2 | 5/2011 | Yoshida et al. | |
| 7,959,559 B2 | 6/2011 | Yamaya | |
| 7,963,911 B2 | 6/2011 | Turliuc | |
| 8,012,084 B2 | 9/2011 | Machida | |
| 8,092,372 B2 | 1/2012 | Machida | |
| 8,096,942 B2 | 1/2012 | Yoshida et al. | |
| 8,109,903 B2 | 2/2012 | Terliuc et al. | |
| 8,147,401 B2 | 4/2012 | Yamaya | |
| 8,187,173 B2 | 5/2012 | Miyoshi | |
| 8,337,395 B2 | 12/2012 | Suzuki et al. | |
| 8,403,827 B2 | 3/2013 | Matsui et al. | |
| 8,439,825 B2 | 5/2013 | Sekiguchi | |
| 8,460,179 B2 | 6/2013 | Ikeda et al. | |
| 8,506,479 B2 | 8/2013 | Piskun et al. | |
| 8,523,763 B2 | 9/2013 | Sinai et al. | |
| 8,679,001 B2 | 3/2014 | Sinai et al. | |
| 8,932,211 B2 | 1/2015 | Piskun et al. | |
| 8,979,884 B2 * | 3/2015 | Milsom | A61B 1/00082 606/191 |
| 9,125,636 B2 | 9/2015 | Piskun et al. | |
| 9,161,746 B2 | 10/2015 | Piskun et al. | |
| 9,186,130 B2 | 11/2015 | Piskun et al. | |
| 9,186,131 B2 | 11/2015 | Piskun et al. | |
| 9,554,690 B2 | 1/2017 | Piskun et al. | |
| 9,565,998 B2 | 2/2017 | Piskun et al. | |
| 9,655,506 B2 | 5/2017 | Piskun et al. | |
| 9,713,416 B2 | 7/2017 | Piskun et al. | |
| 9,737,194 B2 | 8/2017 | Piskun et al. | |
| 9,986,893 B2 * | 6/2018 | Cornhill | A61B 1/00082 |
| 2002/0013601 A1 | 1/2002 | Nobles et al. | |
| 2002/0120180 A1 | 8/2002 | Speier et al. | |
| 2003/0225433 A1 | 12/2003 | Nakao | |
| 2004/0102681 A1 | 5/2004 | Gross | |
| 2004/0186349 A1 | 9/2004 | Ewers et al. | |
| 2004/0210116 A1 | 10/2004 | Nakao | |
| 2004/0260150 A1 | 12/2004 | Bernstein | |
| 2004/0260333 A1 | 12/2004 | Dubrul et al. | |
| 2005/0033363 A1 | 2/2005 | Bojarski et al. | |
| 2005/0033401 A1 | 2/2005 | Cunniffe et al. | |
| 2005/0107664 A1 | 5/2005 | Kalloo et al. | |
| 2005/0165432 A1 | 7/2005 | Heinrich | |
| 2005/0215855 A1 | 9/2005 | Machida | |
| 2005/0277809 A1 | 12/2005 | Takano et al. | |
| 2006/0106288 A1 | 5/2006 | Roth et al. | |
| 2006/0161044 A1 | 7/2006 | Oneda et al. | |
| 2006/0183974 A1 | 8/2006 | Levy et al. | |
| 2006/0189845 A1 | 8/2006 | Maahs et al. | |
| 2006/0241345 A1 | 10/2006 | Oishi et al. | |
| 2006/0258972 A1 | 11/2006 | Mangiardi et al. | |
| 2007/0049797 A1 | 3/2007 | Yoshida et al. | |
| 2007/0106302 A1 | 5/2007 | Ortiz | |
| 2007/0142706 A1 | 6/2007 | Matsui et al. | |
| 2007/0167682 A1 | 7/2007 | Goldfarb et al. | |
| 2007/0215162 A1 | 9/2007 | Glassenberg et al. | |
| 2007/0244361 A1 | 10/2007 | Ikeda et al. | |
| 2007/0265499 A1 | 11/2007 | Wood | |
| 2007/0276181 A1 | 11/2007 | Terliuc | |
| 2007/0282166 A1 | 12/2007 | Ayala et al. | |
| 2008/0065116 A1 | 3/2008 | Lee et al. | |
| 2008/0086155 A1 | 4/2008 | Rothe et al. | |
| 2008/0091063 A1 | 4/2008 | Terliuc | |
| 2008/0091068 A1 | 4/2008 | Terliuc | |
| 2008/0161645 A1 | 7/2008 | Goldwasser et al. | |
| 2008/0200756 A1 | 8/2008 | Okada et al. | |
| 2008/0249358 A1 | 10/2008 | Motai et al. | |

(56) References Cited

U.S. PATENT DOCUMENTS

| | | |
|---|---|---|
| 2009/0156896 A1 | 6/2009 | Kura |
| 2009/0156996 A1 | 6/2009 | Milsom et al. |
| 2009/0187069 A1 | 7/2009 | Terliuc et al. |
| 2009/0203995 A1 | 8/2009 | Matonick |
| 2009/0227835 A1* | 9/2009 | Terliuc ............... A61B 1/00082 600/106 |
| 2009/0234188 A1 | 9/2009 | Matsuura |
| 2009/0287051 A1 | 11/2009 | Itoi |
| 2009/0287058 A1 | 11/2009 | Terliuc |
| 2010/0010530 A1 | 1/2010 | Rhee |
| 2010/0049162 A1 | 2/2010 | Hameed |
| 2010/0105983 A1 | 4/2010 | Oneda et al. |
| 2010/0168510 A1 | 7/2010 | Rogers et al. |
| 2010/0217078 A1 | 8/2010 | Yamakawa et al. |
| 2010/0217185 A1 | 8/2010 | Terliuc et al. |
| 2011/0009863 A1 | 1/2011 | Marczyk et al. |
| 2011/0054253 A1 | 3/2011 | Albiñana et al. |
| 2011/0092770 A1 | 4/2011 | Matsui et al. |
| 2011/0092963 A1 | 4/2011 | Castro |
| 2011/0112410 A1 | 5/2011 | Hirota |
| 2011/0160536 A1 | 6/2011 | Blum |
| 2011/0172491 A1 | 7/2011 | Piskun et al. |
| 2011/0190583 A1 | 8/2011 | Ashida et al. |
| 2011/0245858 A1 | 10/2011 | Milsom et al. |
| 2011/0251555 A1 | 10/2011 | Ducharme et al. |
| 2012/0130170 A1 | 5/2012 | Terliuc |
| 2012/0136343 A1 | 5/2012 | Burnett |
| 2012/0150210 A1 | 6/2012 | Fan et al. |
| 2012/0157771 A1 | 6/2012 | Avitsian et al. |
| 2012/0178994 A1 | 7/2012 | Schembre |
| 2012/0232347 A1 | 9/2012 | Fujikura et al. |
| 2013/0116549 A1 | 5/2013 | Gunday et al. |
| 2013/0144118 A1 | 6/2013 | Piskun et al. |
| 2013/0165942 A1 | 6/2013 | Tan-Malecki et al. |
| 2013/0217957 A1 | 8/2013 | Maahs et al. |
| 2013/0267936 A1 | 10/2013 | Stroup et al. |
| 2013/0345519 A1 | 12/2013 | Piskun et al. |
| 2014/0188159 A1 | 7/2014 | Steege |
| 2015/0018616 A1 | 1/2015 | Kumoyama |
| 2015/0133774 A1 | 5/2015 | Milsorn et al. |
| 2015/0150436 A1 | 6/2015 | Cornhill et al. |
| 2015/0157192 A1 | 6/2015 | Piskun et al. |
| 2015/0164524 A1 | 6/2015 | Malkowski et al. |
| 2015/0209024 A1 | 7/2015 | Piskun et al. |
| 2015/0265818 A1 | 9/2015 | Piskun et al. |
| 2015/0272564 A1 | 10/2015 | Piskun et al. |
| 2015/0282800 A1 | 10/2015 | Piskun et al. |
| 2015/0297209 A1 | 10/2015 | Piskun et al. |
| 2015/0313584 A1 | 11/2015 | Piskun et al. |
| 2015/0335229 A1 | 11/2015 | Terliuc |
| 2016/0015252 A1 | 1/2016 | Piskun et al. |
| 2016/0029875 A1 | 2/2016 | Okada |
| 2016/0089002 A1 | 3/2016 | Burton et al. |
| 2016/0278626 A1 | 9/2016 | Cornhill et al. |
| 2016/0278757 A1 | 9/2016 | Piskun et al. |
| 2016/0309996 A1 | 10/2016 | Piskun et al. |
| 2016/0310124 A1 | 10/2016 | Piskun et al. |
| 2016/0338572 A1 | 11/2016 | Piskun et al. |
| 2016/0374658 A1 | 12/2016 | Piskun |
| 2017/0079636 A1 | 3/2017 | Piskun et al. |
| 2017/0105726 A1 | 4/2017 | Smith et al. |
| 2017/0135567 A1 | 5/2017 | Piskun et al. |
| 2018/0035872 A1 | 2/2018 | Cruz et al. |

FOREIGN PATENT DOCUMENTS

| | | |
|---|---|---|
| CN | 1647747 A | 8/2005 |
| CN | 105832279 | 8/2016 |
| EP | 0 402 467 | 12/1990 |
| EP | 1 654 977 | 5/2006 |
| EP | 1 782 726 | 5/2007 |
| EP | 2 026 866 | 2/2009 |
| EP | 1 977 679 | 8/2010 |
| EP | 1 731 084 | 12/2010 |
| EP | 2 364 637 | 9/2011 |
| EP | 1 718 193 | 7/2013 |
| JP | 3-258268 | 11/1991 |
| JP | 6-113998 | 4/1994 |
| JP | 7-308388 | 11/1995 |
| JP | 2000-033071 | 2/2000 |
| JP | 2000-037347 | 2/2000 |
| JP | 2004-016728 | 1/2004 |
| JP | 2007-296054 | 11/2007 |
| JP | 2011-087647 | 5/2011 |
| JP | 2012-029886 | 2/2012 |
| WO | WO 1989/007413 | 8/1989 |
| WO | WO 2001/054568 | 8/2001 |
| WO | WO 2002/087495 | 11/2002 |
| WO | WO 2003/103517 | 12/2003 |
| WO | WO 2004/060463 | 7/2004 |
| WO | WO 2005/074377 | 8/2005 |
| WO | WO 2005/089627 | 9/2005 |
| WO | WO 2005/110204 | 11/2005 |
| WO | WO 2006/138013 | 12/2006 |
| WO | WO 2007/017854 | 2/2007 |
| WO | WO 2007/135665 | 11/2007 |
| WO | WO 2008/004228 | 1/2008 |
| WO | WO 2008/044615 | 4/2008 |
| WO | WO 2008/142685 | 11/2008 |
| WO | WO 2009/027394 | 3/2009 |
| WO | WO 2009/122395 | 10/2009 |
| WO | WO 2010/091440 | 8/2010 |
| WO | WO 2011/004820 | 1/2011 |
| WO | WO 2014/190026 | 11/2014 |
| WO | WO 2015/064616 | 5/2015 |
| WO | WO 2015/123313 | 8/2015 |
| WO | WO 2016/186876 | 11/2016 |
| WO | WO 2016/193820 | 12/2016 |
| WO | WO 2017/066063 | 4/2017 |

* cited by examiner

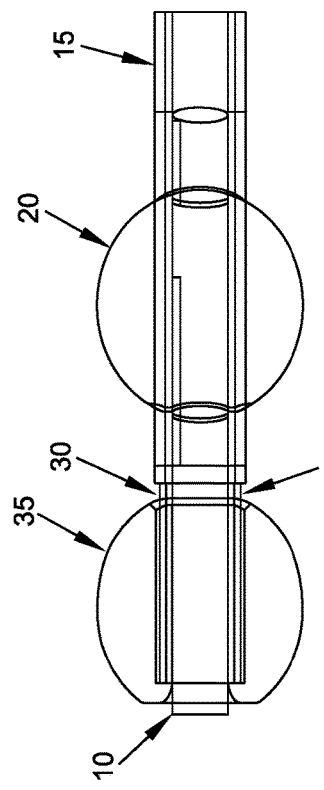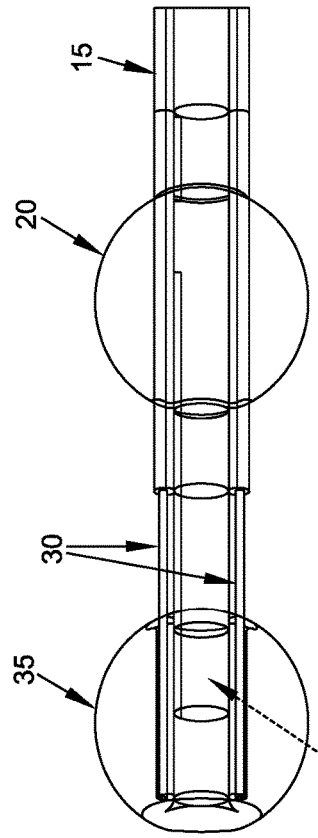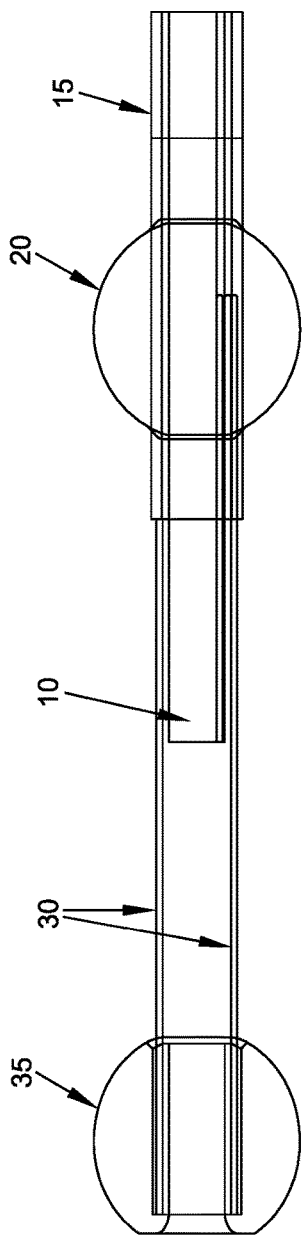

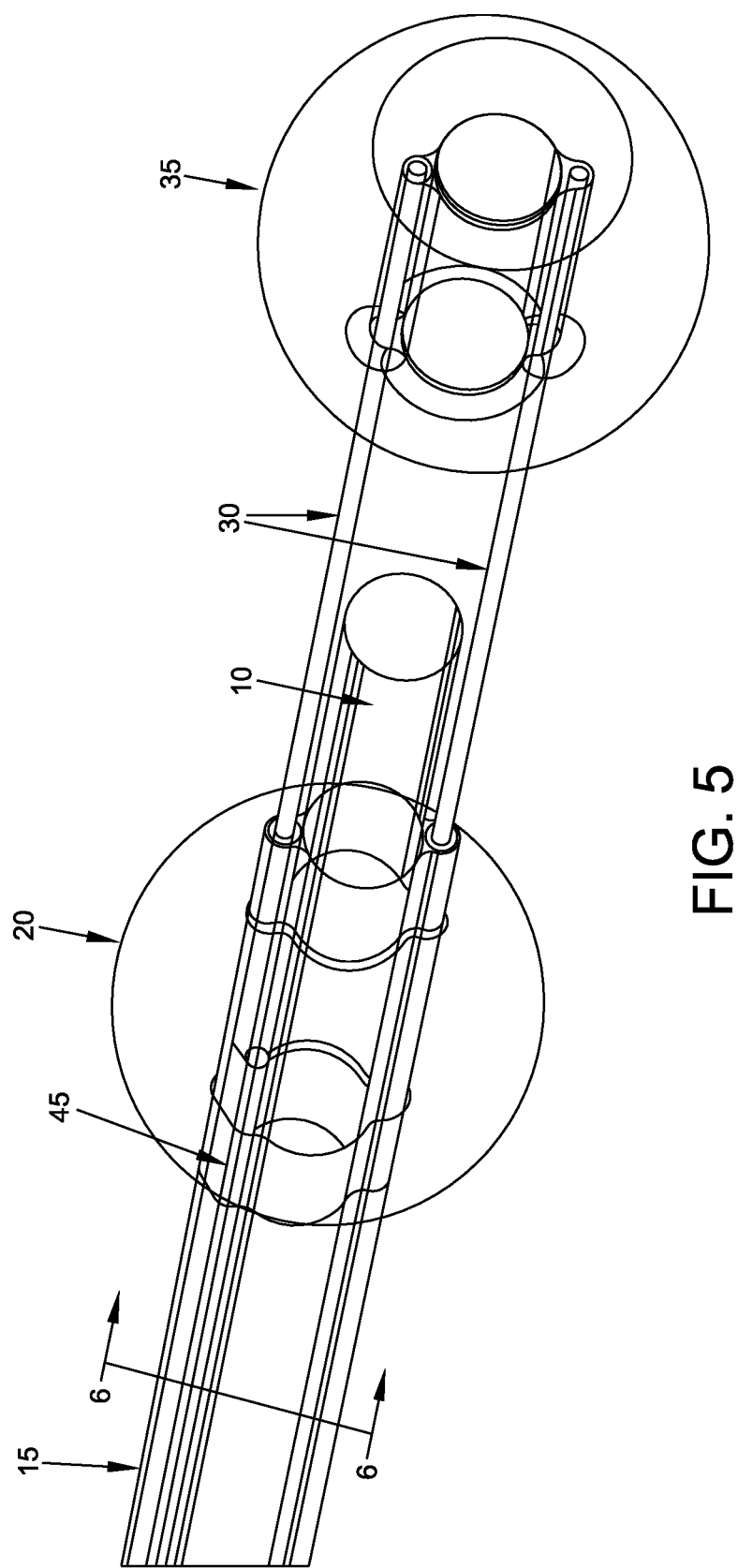

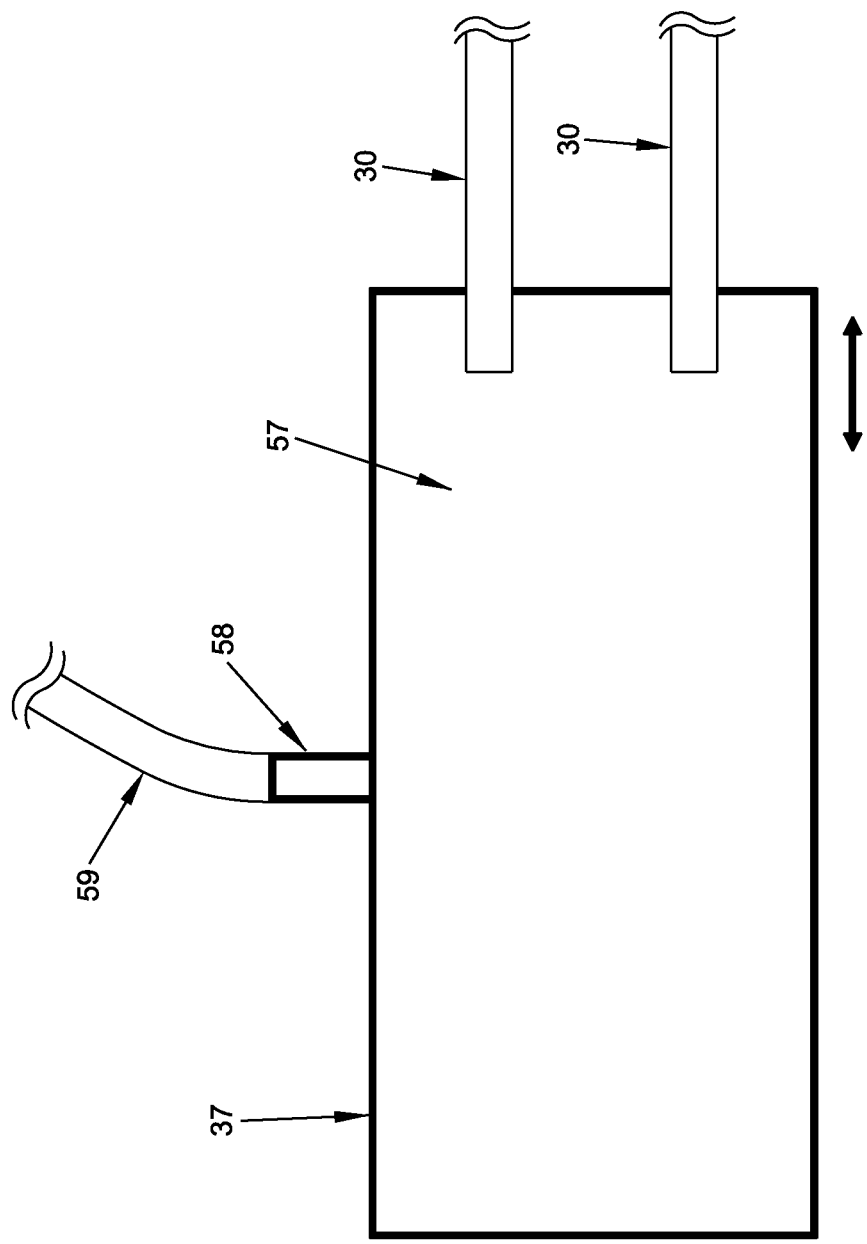

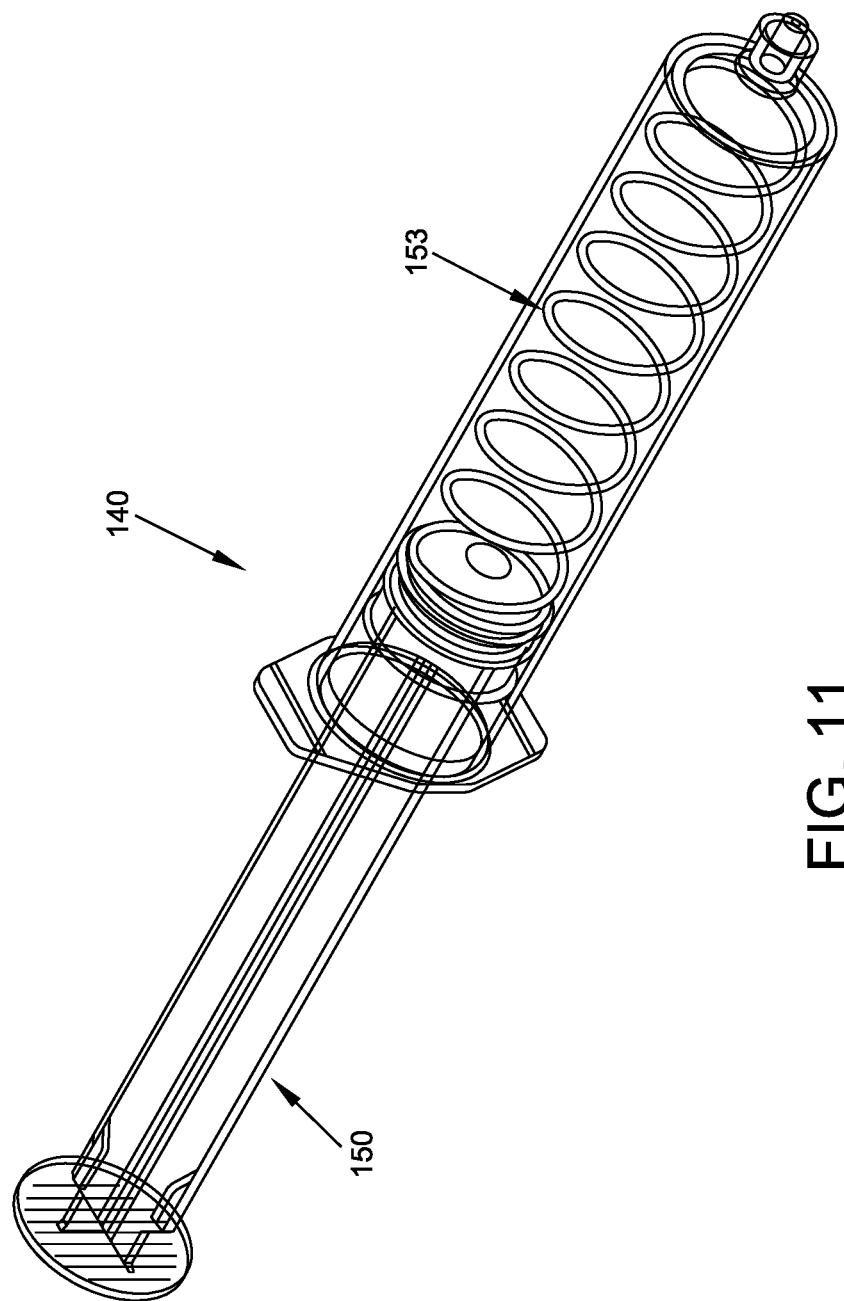

INSERT SCOPE INTO PATIENT

ADVANCE TO DESIRE LOCATION (TOP VIEW)

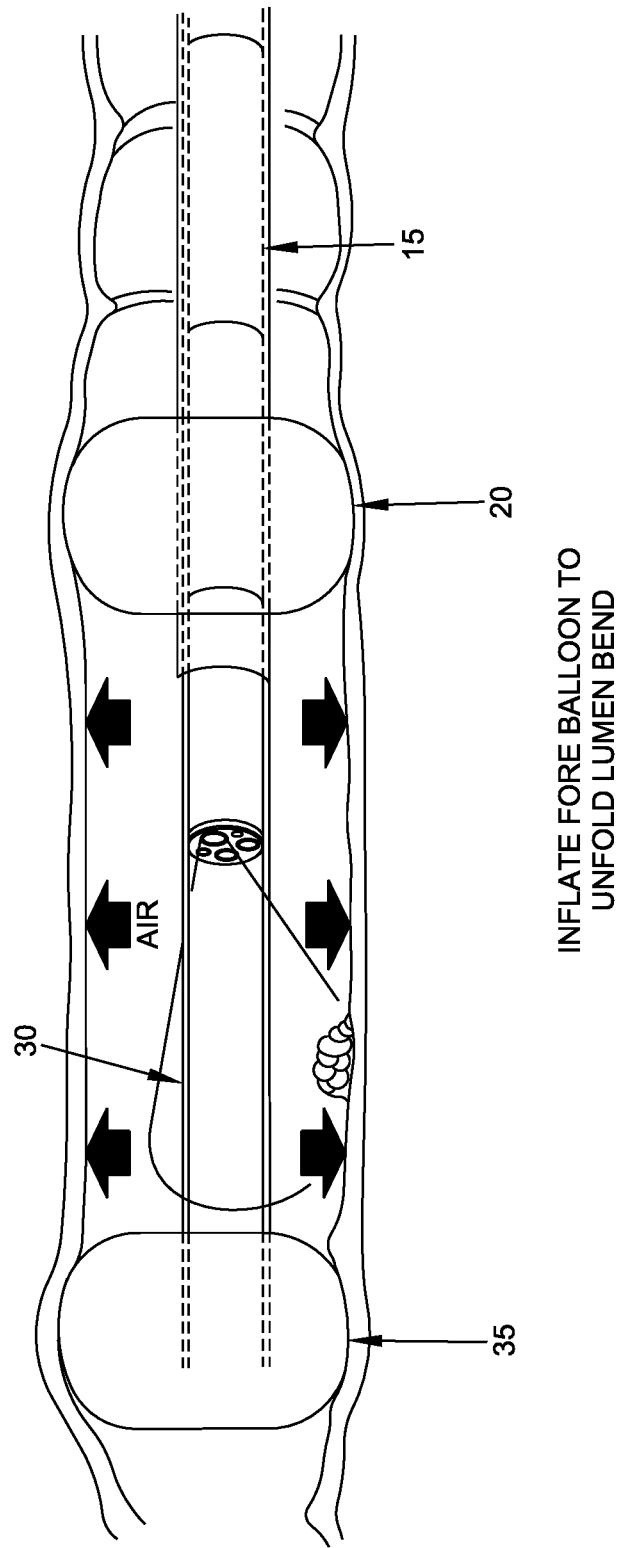

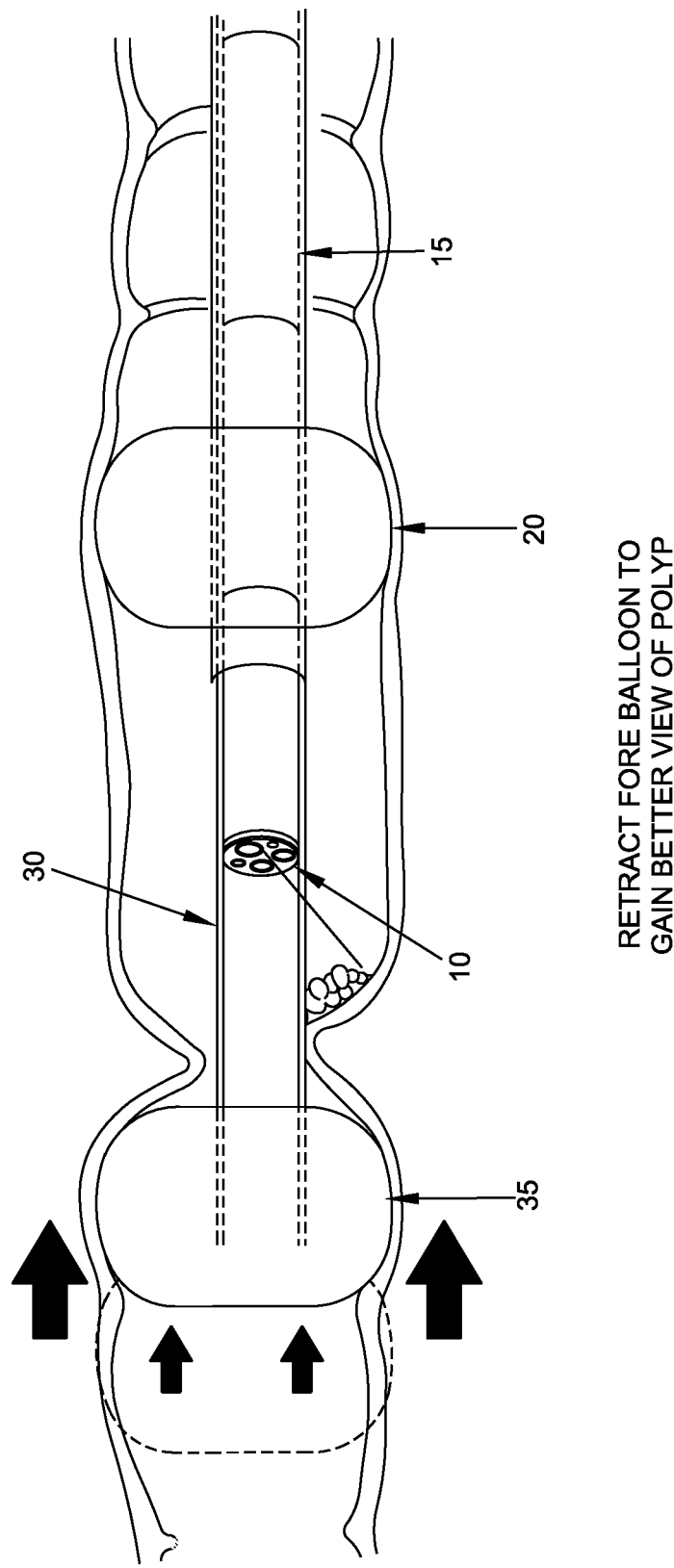

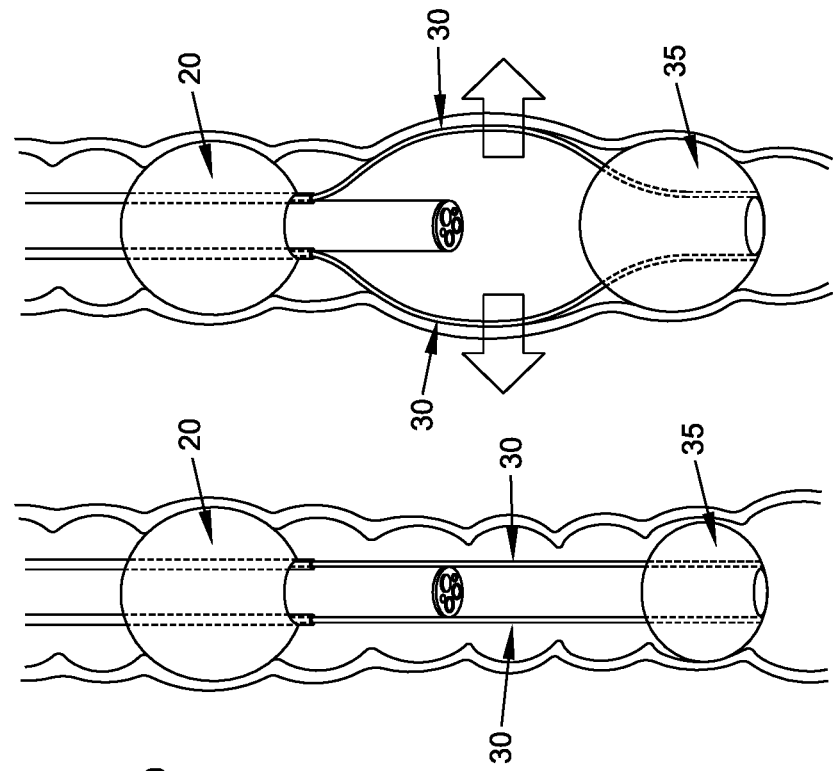
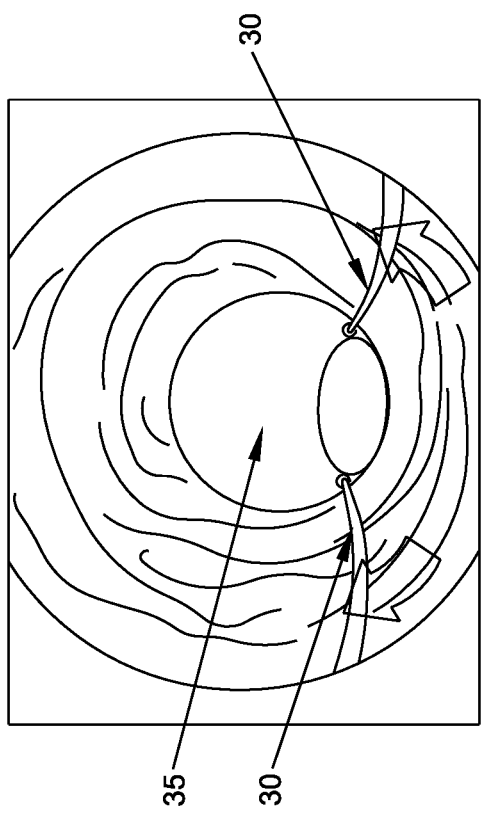
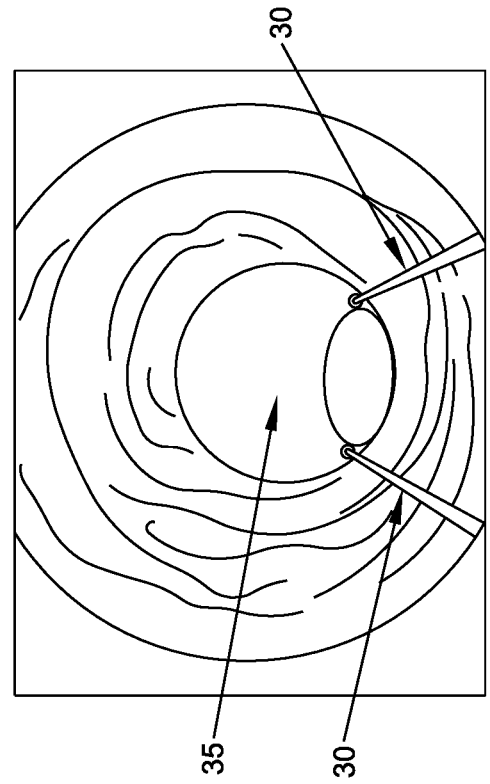
FIG. 22A  FIG. 22B  FIG. 22C  FIG. 22D

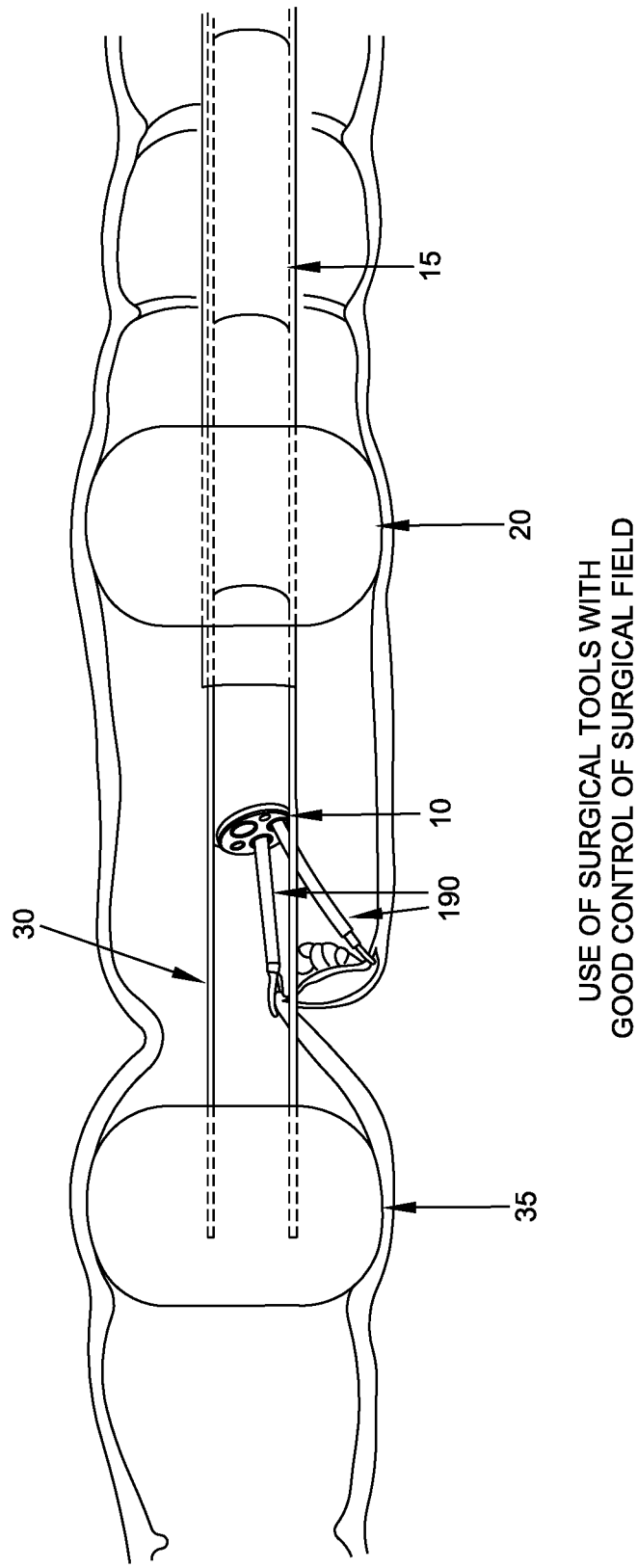

ISOLATED THERAPEUTIC ZONE ENABLES RAPID FLUSHING FOR IDENTIFICATION OF BLEEDING SITES

SEALED ZONE IS FILLED WITH
FLUID VIA WORKING CHANNEL

SUCTIONING OUT FLUID FOR
FURTHER EVALUATION OF BLEEDING

BLEEDING POINT CONTROLLED BY BALLOON PRESSURE

INFLATED FORE BALLOON USED AS BRAKE

SCOPE WITHDRAWAL PASSING THROUGH SECTION DEF

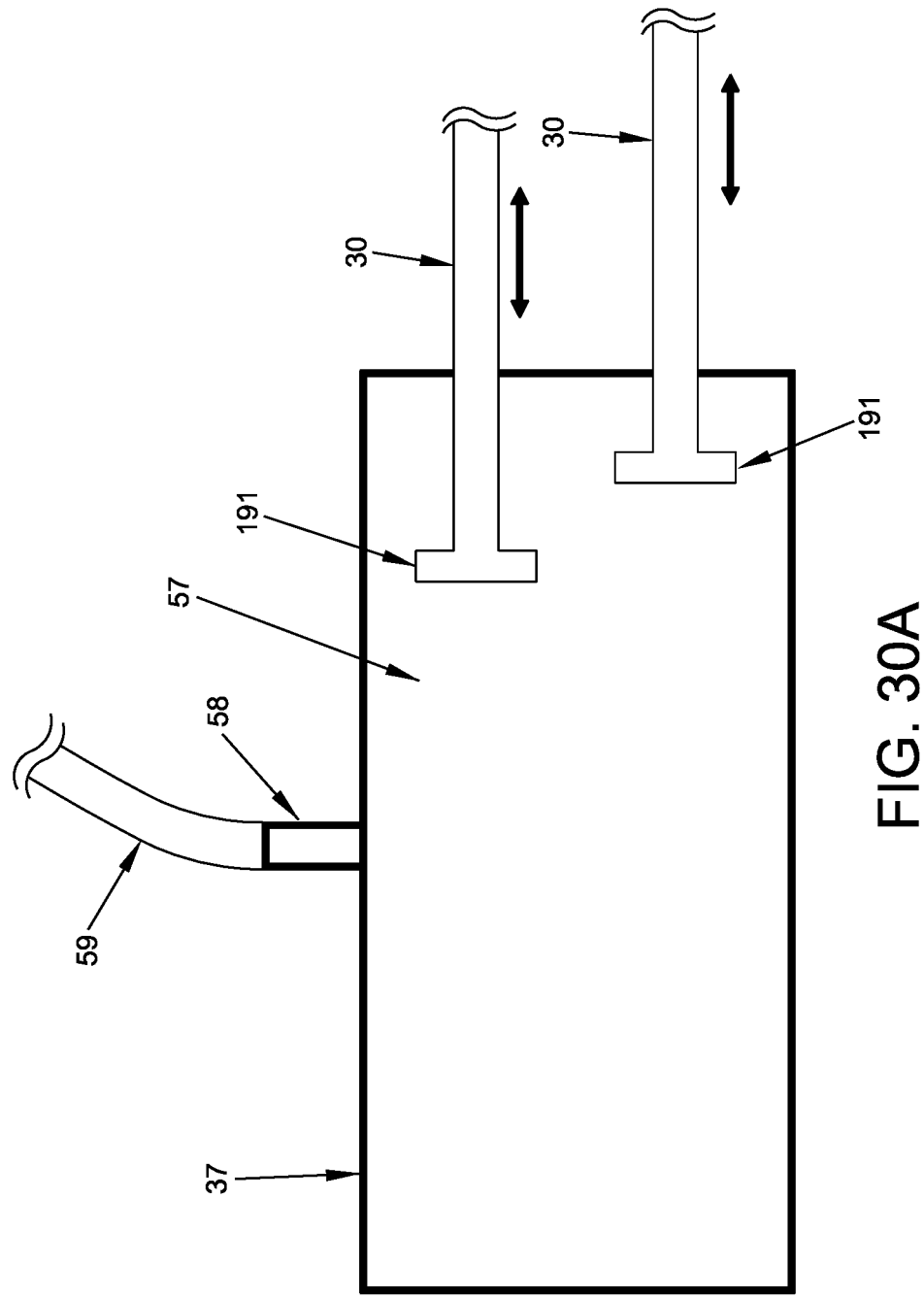

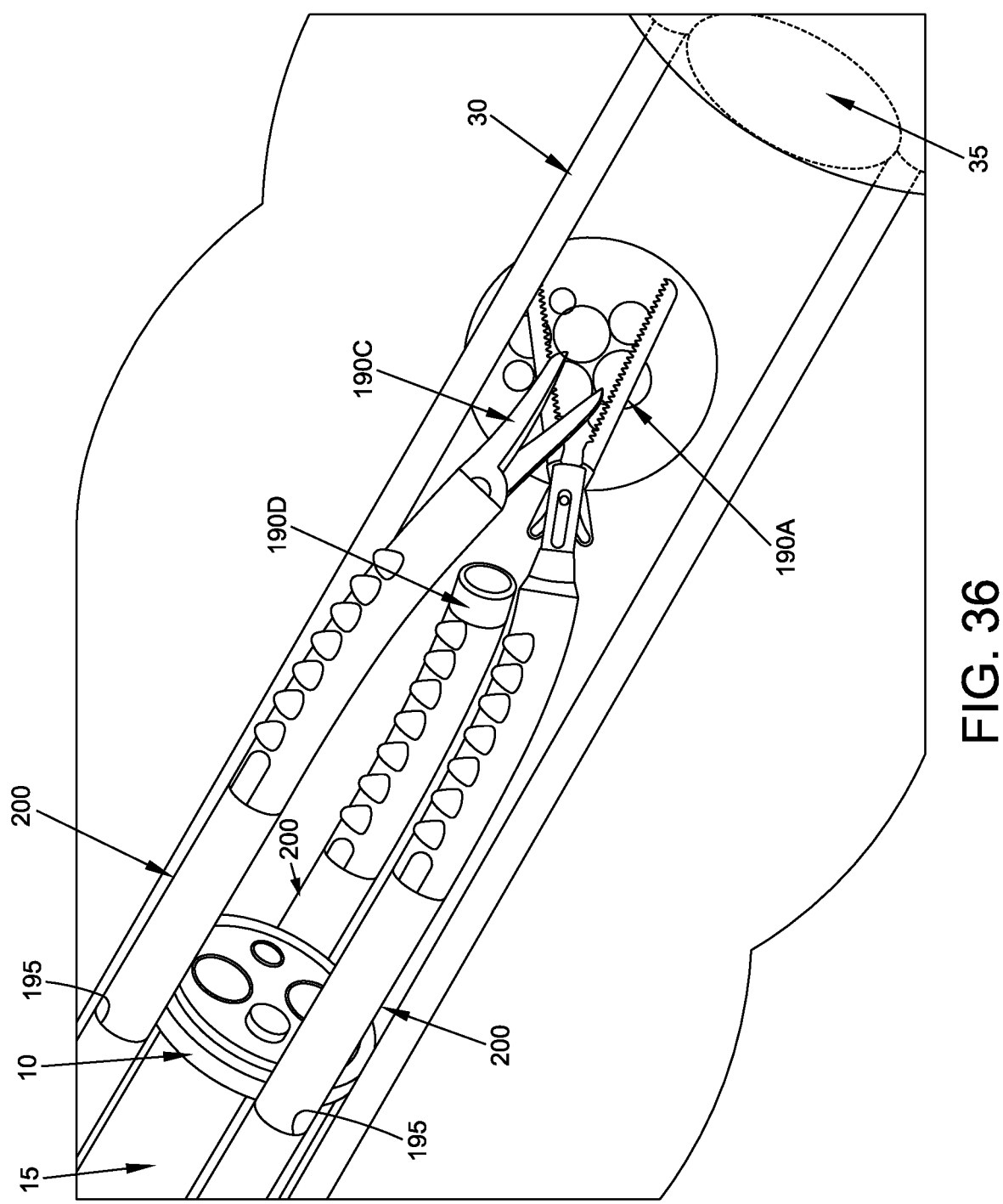

METHOD AND APPARATUS FOR MANIPULATING THE SIDE WALL OF A BODY LUMEN OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME

REFERENCE TO PENDING PRIOR PATENT APPLICATIONS

This patent application is a continuation of pending prior U.S. patent application Ser. No. 14/619,845, filed Feb. 11, 2015 by Cornell University for METHOD AND APPARATUS FOR MANIPULATING THE SIDE WALL OF A BODY LUMEN OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME, which patent application in turn:

(i) is a continuation-in-part of prior U.S. patent application Ser. No. 14/540,355, filed Nov. 13, 2014 by Cornell University and Jeffrey Milsom et al. for METHOD AND APPARATUS FOR STABILIZING, STRAIGHTENING, EXPANDING AND/OR FLATTENING THE SIDE WALL OF A BODY LUMEN AND/OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME, which patent application is a continuation of prior U.S. patent application Ser. No. 12/969,059, filed Dec. 15, 2010 by Jeffrey Milsom et al. for METHOD AND APPARATUS FOR STABILIZING, STRAIGHTENING, EXPANDING AND/OR FLATTENING THE SIDE WALL OF A BODY LUMEN AND/OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME, which patent application claims benefit of prior U.S. Provisional Patent Application Ser. No. 61/284,215, filed Dec. 15, 2009 by Jeffrey Milsom et al. for METHOD AND APPARATUS FOR STABILIZING, STRAIGHTENING, EXPANDING AND/OR FLATTENING THE SIDE WALL OF A BODY LUMEN OR BODY CAVITY SO AS TO PROVIDE INCREASED VISUALIZATION OF THE SIDE WALL OF THE BODY LUMEN OR BODY CAVITY, AND/OR FOR STABILIZING INSTRUMENTS RELATIVE TO THE SAME; and (ii) claims benefit of prior U.S. Provisional Patent Application Ser. No. 61/938,446, filed Feb. 11, 2014 by Cornell University and John Frederick Cornhill et al. for METHOD AND APPARATUS FOR MANIPULATING THE SIDE WALL OF A BODY LUMEN OR BODY CAVITY SO AS TO PROVIDE INCREASED VISUALIZATION OF THE SAME AND/OR INCREASED ACCESS TO THE SAME, AND/OR FOR STABILIZING INSTRUMENTS RELATIVE TO THE SAME.

The five (5) above-identified patent applications are hereby incorporated herein by reference.

FIELD OF THE INVENTION

This invention relates to surgical methods and apparatus in general, and more particularly to surgical methods and apparatus for manipulating the side wall of a body lumen and/or body cavity so as to provide increased visualization of the same and/or increased access to the same, and/or for stabilizing instruments relative to the same.

BACKGROUND OF THE INVENTION

The human body comprises many different body lumens and body cavities. By way of example but not limitation, the human body comprises body lumens such as the gastrointestinal (GI) tract, blood vessels, lymphatic vessels, the urinary tract, fallopian tubes, bronchi, bile ducts, etc. By way of further example but not limitation, the human body comprises body cavities such as the head, chest, abdomen, nasal sinuses, bladder, cavities within organs, etc.

In many cases it may be desirable to endoscopically examine and/or treat a disease process or abnormality which is located within, or on the side wall of, a body lumen and/or body cavity. By way of example but not limitation, it may be desirable to examine the side wall of the gastrointestinal tract for lesions and, if a lesion is found, to biopsy, remove and/or otherwise treat the lesion.

The endoscopic examination and/or treatment of the side wall of a body lumen and/or body cavity can be complicated by the anatomic configuration (both regional and local) of the side wall of the body lumen and/or body cavity, and/or by the consistency of the tissue making up the side wall of the body lumen and/or body cavity, and/or by the tethering of the side wall of the body lumen and/or body cavity to other anatomical structures.

By way of example but not limitation, the intestine is an elongated tubular organ having an inner lumen and is characterized by frequent turns (i.e., the regional anatomic configuration of the intestine) and a side wall characterized by numerous folds (i.e., the local anatomic configuration of the intestine), with the side wall tissue having a relatively soft, pliable consistency, and with the colon in particular being tethered to the abdomen and/or other abdominal structures via soft tissue. It can be difficult to fully visualize the side wall of the intestine, and/or to treat a lesion formed on the side wall of the intestine, due to this varying side wall anatomic configuration (both regional and local), its relatively soft, pliable consistency, and its tethering to other anatomical structures via soft tissue. By way of example but not limitation, in the case of colonoscopies, it has been found that approximately 5-40% of patients have an anatomic configuration (regional and/or local) of the side wall, and/or a tissue consistency, and/or colon tethering to other anatomical structures, which makes it difficult to fully visualize the anatomy (including pathologic conditions of that anatomy, such as polyps or tumors) using conventional endoscopes, and/or to fully access the anatomy using instruments introduced through conventional endoscopes.

In addition to the foregoing, it has also been found that some body lumens and/or body cavities can spasm and/or contract spontaneously but especially when an endoscope or other instrument is inserted into the body lumen and/or body cavity. This spasming and/or contraction can cause the body lumen and/or body cavity to constrict and/or otherwise move and/or change its configuration, which can further complicate and/or compromise endoscopic visualization of the anatomy, and/or further complicate and/or compromise access to the anatomy using instruments introduced through conventional, flexible endoscopes. In addition, during examination of the colon, which is typically conducted while both inserting and withdrawing the endoscope through the colon, the endoscope may grip and/or otherwise gather the colon during insertion and withdrawal and then suddenly slip and release the colon. This results in the endoscope moving quickly past significant lengths of the colon, thereby making accurate examination of the colon challenging.

It would, therefore, be highly advantageous to provide novel apparatus capable of manipulating the side wall of a body lumen and/or body cavity so as to better present the side wall tissue (including visualization of areas initially hidden or outside the field of view) for examination and/or treatment during an endoscopic procedure.

It would also be highly advantageous to provide novel apparatus capable of steadying and/or stabilizing the distal tips and/or working ends of instruments (e.g., endoscopes, articulating and/or non-articulating devices such as graspers, cutters or dissectors, cauterizing tools, ultrasound probes, etc.) inserted into a body lumen and/or body cavity with respect to the side wall of the body lumen and/or body cavity, whereby to facilitate the precision use of those instruments.

Among other things, it would be highly advantageous to provide novel apparatus capable of steadying and/or stabilizing the distal tips and/or working ends of endoscopes (and hence also steadying and/or stabilizing the distal tips and/or working ends of other instruments inserted through the working channels of those endoscopes, such as graspers, cutters or dissectors, cauterizing tools, ultrasound probes, etc.).

And it would be highly advantageous to provide novel apparatus capable of steadying and/or stabilizing the distal tips and/or working ends of instruments (such as graspers, cutters or dissectors, cauterizing tools, ultrasound probes, etc.) advanced to the surgical site by means other than through the working channels of endoscopes.

It would also be highly advantageous to be able to straighten bends, "iron out" inner luminal surface folds and create a substantially static or stable side wall of the body lumen and/or body cavity, whereby to enable more precise visual examination (including visualization of areas initially hidden or outside the field of view) and/or therapeutic intervention.

SUMMARY OF THE INVENTION

The present invention comprises the provision and use of novel apparatus for manipulating the side wall of a body lumen and/or body cavity so as to better present the side wall tissue (including visualization of areas initially hidden or outside the field of view) for examination and/or treatment during an endoscopic procedure.

The present invention also comprises the provision and use of novel apparatus capable of steadying and/or stabilizing the distal tips and/or working ends of instruments (e.g., endoscopes, articulating and/or non-articulating devices such as graspers, cutters or dissectors, cauterizing tools, ultrasound probes, etc.) inserted into a body lumen and/or body cavity with respect to the side wall of the body lumen and/or body cavity, whereby to facilitate the precision use of those instruments.

Among other things, the present invention comprises the provision and use of novel apparatus capable of steadying and/or stabilizing the distal tips and/or working ends of endoscopes (and hence also steadying and/or stabilizing the distal tips and/or working ends of other instruments inserted through the working channels of those endoscopes, such as graspers, cutters or dissectors, cauterizing tools, ultrasound probes, etc.).

And the present invention comprises the provision and use of novel apparatus capable of steadying and/or stabilizing the distal tips and/or working ends of instruments (such as graspers, cutters or dissectors, cauterizing tools, ultrasound probes, etc.) advanced to the surgical site by means other than through the working channels of endoscopes.

And the present invention comprises the provision and use of novel apparatus capable of straightening bends, "ironing out" folds and creating a substantially static or stable side wall of the body lumen and/or body cavity which enables more precise visual examination (including visualization of areas initially hidden or outside the field of view) and/or therapeutic intervention.

In one preferred form of the present invention, there is provided apparatus comprising:
  a sleeve adapted to be slid over the exterior of an endoscope;
  a proximal balloon secured to said sleeve;
  an inflation/deflation tube carried by said sleeve and in fluid communication with the interior of said proximal balloon;
  a push tube slidably mounted to said sleeve; and
  a distal balloon secured to the distal end of said push tube, the interior of said distal balloon being in fluid communication with said push tube, wherein said distal balloon is capable of assuming a deflated condition and an inflated condition, and further wherein when said distal balloon is in its deflated condition, an axial opening extends therethrough, said axial opening being sized to receive the endoscope therein, and when said distal balloon is in its inflated condition, said axial opening is closed down.

In another preferred form of the present invention, there is provided a method for performing a procedure in a body lumen and/or body cavity, said method comprising:
  providing apparatus comprising:
    a sleeve adapted to be slid over the exterior of an endoscope;
    a proximal balloon secured to said sleeve;
    an inflation/deflation tube carried by said sleeve and in fluid communication with the interior of said proximal balloon;
    a push tube slidably mounted to said sleeve; and
    a distal balloon secured to the distal end of said push tube, the interior of said distal balloon being in fluid communication with said push tube, wherein said distal balloon is capable of assuming a deflated condition and an inflated condition, and further wherein when said distal balloon is in its deflated condition, an axial opening extends therethrough, said axial opening being sized to receive the endoscope therein, and when said distal balloon is in its inflated condition, said axial opening is closed down;
  positioning said apparatus in the body lumen and/or body cavity;
  inflating said proximal balloon;
  advancing said push tube distally;
  inflating said distal balloon; and
  performing the procedure.

In another preferred form of the present invention, there is provided apparatus comprising:
  a sleeve adapted to be slid over the exterior of an endoscope, said sleeve comprising a passageway formed integral with said sleeve and a lumen formed integral with said sleeve for receiving an instrument;
  a proximal balloon secured to said sleeve;
  an inflation/deflation tube carried by said sleeve and in fluid communication with the interior of said proximal balloon;
  a push tube slidably mounted in said passageway of said sleeve; and a distal balloon secured to the distal end of said push tube, the interior of said distal balloon being in fluid communication with said push tube.

In another preferred form of the present invention, there is provided a method for performing a procedure in a body lumen and/or body cavity, said method comprising:
   providing apparatus comprising:
      a sleeve adapted to be slid over the exterior of an endoscope, said sleeve comprising a passageway formed integral with said sleeve and a lumen formed integral with said sleeve for receiving an instrument;
      a proximal balloon secured to said sleeve;
      an inflation/deflation tube carried by said sleeve and in fluid communication with the interior of said proximal balloon;
      a push tube slidably mounted in said passageway of said sleeve; and
      a distal balloon secured to the distal end of said push tube, the interior of said distal balloon being in fluid communication with said push tube;
   positioning said apparatus in the body lumen and/or body cavity;
   inflating said proximal balloon;
   advancing said push tube distally;
   inflating said distal balloon; and
   performing the procedure.

In another preferred form of the present invention, there is provided apparatus comprising:
   a sleeve adapted to be slid over the exterior of an endoscope so as to substantially cover the endoscope from a point adjacent to the distal end of the endoscope to a point adjacent to the handle of the endoscope;
   a proximal balloon secured to said sleeve;
   an inflation/deflation tube carried by said sleeve and in fluid communication with the interior of said proximal balloon;
   a push tube slidably mounted to said sleeve; and
   a distal balloon secured to the distal end of said push tube, the interior of said distal balloon being in fluid communication with said push tube.

In another preferred form of the present invention, there is provided a method for performing a procedure in a body lumen and/or body cavity, said method comprising:
   providing apparatus comprising:
      a sleeve adapted to be slid over the exterior of an endoscope so as to substantially cover the endoscope from a point adjacent to the distal end of the endoscope to a point adjacent to the handle of the endoscope;
      a proximal balloon secured to said sleeve;
      an inflation/deflation tube carried by said sleeve and in fluid communication with the interior of said proximal balloon;
      a push tube slidably mounted to said sleeve; and
      a distal balloon secured to the distal end of said push tube, the interior of said distal balloon being in fluid communication with said push tube;
   positioning said apparatus in the body lumen and/or body cavity;
   inflating said proximal balloon;
   advancing said push tube distally;
   inflating said distal balloon; and
   performing the procedure.

In another preferred form of the present invention, there is provided apparatus comprising:
   a sleeve adapted to be slid over the exterior of an endoscope;
   a proximal balloon secured to said sleeve;
   an inflation/deflation tube carried by said sleeve and in fluid communication with the interior of said proximal balloon;
   a pair of push tubes slidably mounted to said sleeve; and
   a distal balloon secured to the distal ends of said pair of push tubes, the interior of said distal balloon being in fluid communication with said pair of push tubes.

In another preferred form of the present invention, there is provided a method for performing a procedure in a body lumen and/or body cavity, said method comprising:
   providing apparatus comprising:
      a sleeve adapted to be slid over the exterior of an endoscope;
      a proximal balloon secured to said sleeve;
      an inflation/deflation tube carried by said sleeve and in fluid communication with the interior of said proximal balloon;
      a pair of push tubes slidably mounted to said sleeve; and
      a distal balloon secured to the distal ends of said pair of push tubes, the interior of said distal balloon being in fluid communication with said pair of push tubes;
   positioning said apparatus in the body lumen and/or body cavity;
   inflating said proximal balloon;
   advancing said pair of push tubes distally;
   inflating said distal balloon; and
   performing the procedure.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts and further wherein:

FIGS. 2-4 are schematic views showing various dispositions of the fore balloon relative to the aft balloon;

FIG. 5 is a schematic view showing further details of the distal end of the apparatus shown in FIG. 1;

FIG. 8A is a schematic view showing the push tube handle;

FIG. 11 is a schematic view showing one form of inflation mechanism provided in accordance with the present invention;

FIGS. 16-30 are schematic views showing preferred ways of using the apparatus of FIG. 1;

FIG. 30A is a schematic view showing an alternative construction for the push tubes and push tube handle of the present invention;

FIG. 36 is a schematic view showing instrument guide tubes which may be disposed in the additional lumens of the sleeve, wherein instruments may be advanced through the instrument guide tubes.

DETAILED DESCRIPTION OF THE PREFERRED EMBODIMENTS

The present invention comprises the provision and use of novel apparatus for manipulating the side wall of a body lumen and/or body cavity so as to better present the side wall tissue (including visualization of areas initially hidden or outside the field of view) for examination and/or treatment during an endoscopic procedure.

(As used herein, the term "endoscopic procedure" is intended to mean substantially any minimally-invasive or limited access procedure, diagnostic and/or therapeutic and/or surgical, for accessing, endoluminally or transluminally or otherwise, the interior of a body lumen and/or body cavity for the purposes of viewing, biopsying and/or treating tissue, including removing a lesion and/or resecting tissue, etc.)

The present invention also comprises the provision and use of novel apparatus capable of steadying and/or stabilizing the distal tips and/or working ends of instruments (e.g., endoscopes, articulating and/or non-articulating devices such as graspers, cutters or dissectors, cauterizing tools, ultrasound probes, etc.) inserted into a body lumen and/or body cavity with respect to the side wall of the body lumen and/or body cavity, whereby to facilitate the precision use of those instruments.

Among other things, the present invention comprises the provision and use of novel apparatus capable of steadying and/or stabilizing the distal tips and/or working ends of endoscopes (and hence also steadying and/or stabilizing the distal tips and/or working ends of other instruments inserted through the working channels of those endoscopes, such as graspers, cutters or dissectors, cauterizing tools, ultrasound probes, etc.).

And the present invention comprises the provision and use of novel apparatus capable of steadying and/or stabilizing the distal tips and/or working ends of instruments (such as graspers, cutters or dissectors, cauterizing tools, ultrasound probes, etc.) advanced to the surgical site by means other than through the working channels of endoscopes.

And the present invention comprises the provision and use of novel apparatus capable of straightening bends, "ironing out" folds and creating a substantially static or stable side wall of the body lumen and/or body cavity which enables more precise visual examination (including visualization of areas initially hidden or outside the field of view) and/or therapeutic intervention.

The Novel Apparatus

Figure 1:
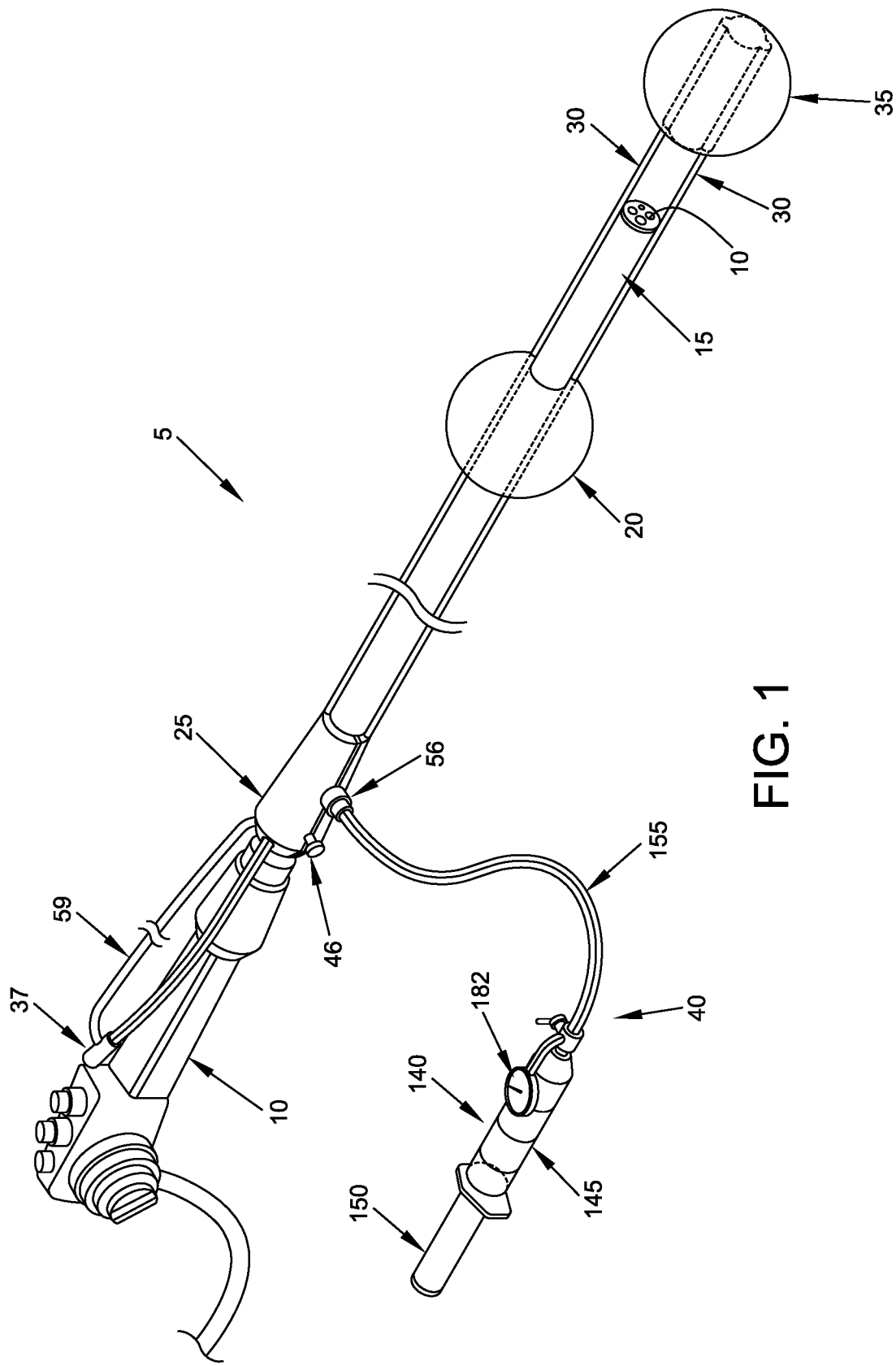
FIG. 1 is a schematic view showing novel apparatus formed in accordance with the present invention, wherein the novel apparatus comprises, among other things, a sleeve for disposition over the end of an endoscope, an aft balloon mounted to the sleeve, a pair of push tubes slidably mounted to the sleeve, a fore balloon mounted to the distal end of the push tubes, and a push tube handle mounted to the proximal ends of the push tubes.
Figure 6:
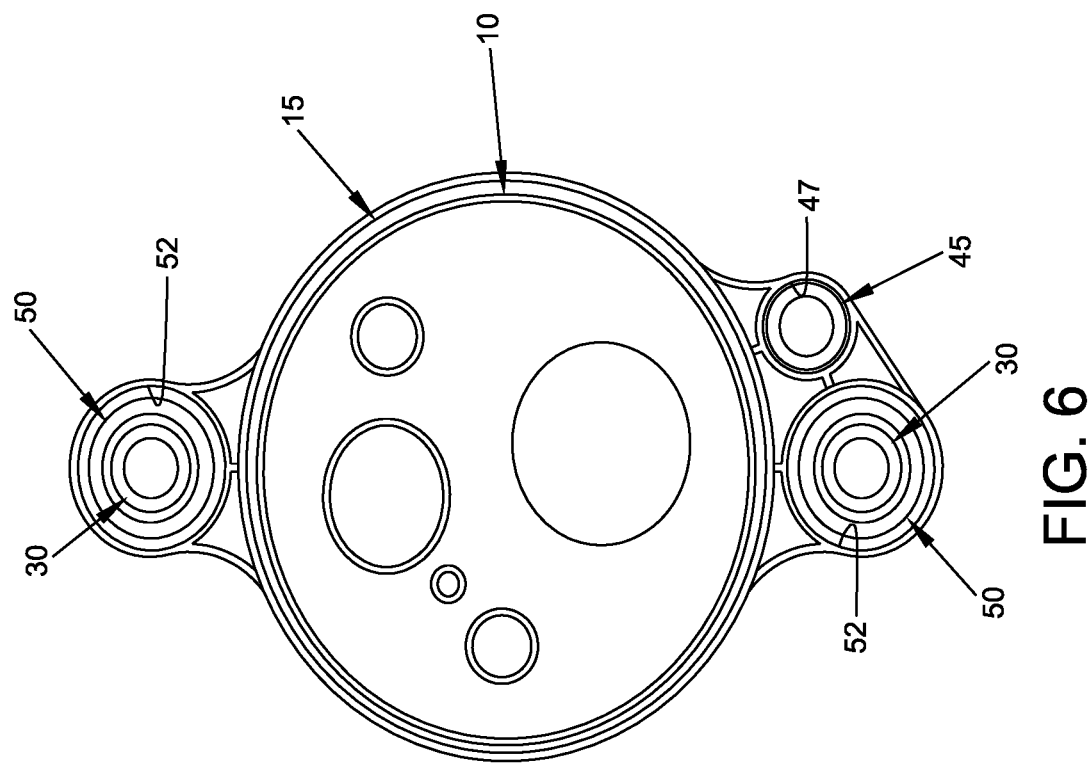
FIG. 6 is a section view taken along line 6-6 of FIG. 5.
Figure 8:
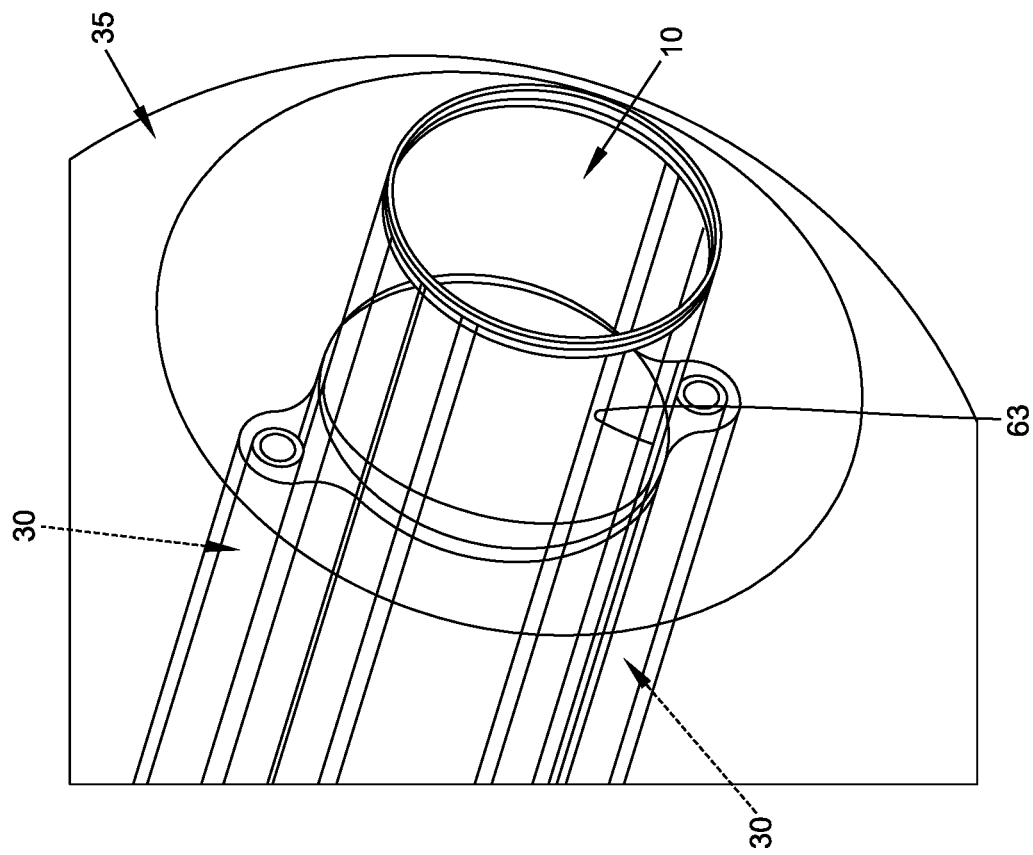
FIGS. 7 and 8 are schematic views showing further details of the fore balloon.
Figure 7:
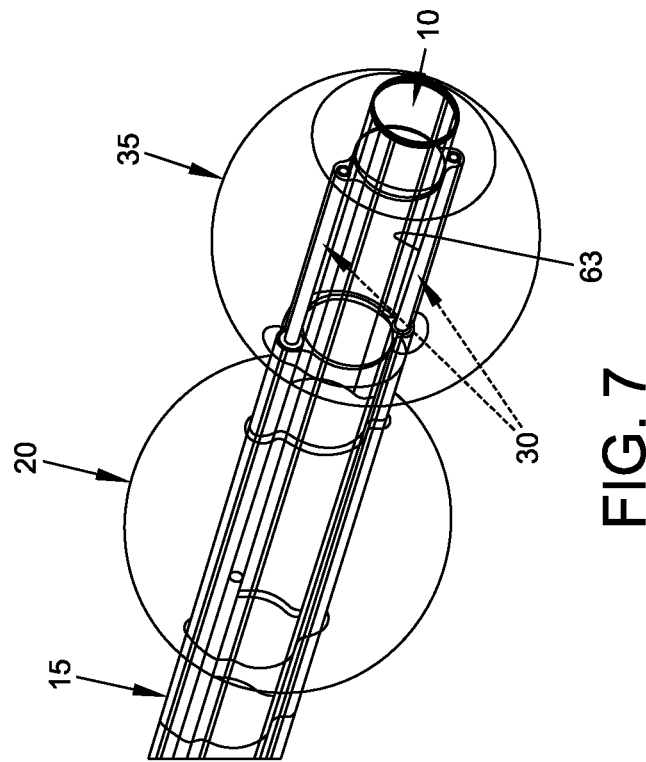

In accordance with the present invention, and looking now at FIG. 1, there is shown novel apparatus 5 which is capable of manipulating (e.g., stabilizing, straightening, expanding and/or flattening, etc.) the side wall of a body lumen and/or body cavity so as to better present the side wall tissue (including visualization of areas initially hidden or outside the field of view) for examination and/or treatment during an endoscopic procedure using an endoscope 10 (e.g., an articulating endoscope), and/or for stabilizing the distal end of endoscope 10 and/or the distal tips and/or working ends of other instruments (e.g., graspers, cutters or dissectors, cauterizing tools, ultrasound probes, etc., not shown in FIG. 1).

More particularly, apparatus 5 generally comprises a sleeve 15 adapted to be slid over the exterior of the shaft of endoscope 10, a proximal (or "aft") balloon 20 (the terms "proximal" and "aft" will hereinafter be used interchangeably) secured to sleeve 15 near the distal end of the sleeve, and a base 25 secured to sleeve 15 at the proximal end of the sleeve. Apparatus 5 also comprises a pair of push tubes 30 slidably mounted to sleeve 15 as will hereinafter be discussed, and a distal (or "fore") balloon 35 (the terms "distal" and "fore" will hereinafter be used interchangeably) secured to the distal ends of push tubes 30, such that the spacing between aft balloon 20 and fore balloon 35 can be adjusted by the physician (or other operator or user) by moving push tubes 30 relative to sleeve 15 (e.g., by advancing the two push tubes simultaneously at push tube handle 37, see below). See FIGS. 1 and 2-4. Apparatus 5 also comprises an associated inflation mechanism 40 (FIG. 1) for enabling selective inflation/deflation of one or both of aft balloon 20 and fore balloon 35 by the physician or (or other operator or user).

Looking now at FIGS. 1-6, sleeve 15 generally comprises an elongated, thin-walled tube configured to be slid over the exterior of the shaft of endoscope 10 (e.g., retrograde from the distal tip of the endoscope) so as to make a close fit therewith, with the sleeve being sized and constructed so that it will slide easily back over the endoscope during mounting thereon (preferably with the scope "dry") but will have sufficient residual friction (when gripped by the hand of the physician or other operator or user) with the outer surface of the endoscope such that the sleeve will remain in place to allow torqueing (i.e., rotational turning) and pushing/pulling of the endoscope during use (e.g., within the colon of a patient). In one preferred form of the invention, sleeve 15 can move circumferentially to some extent about endoscope 10 (and when gripped securely by the hand of the physician or other operator or user, can rotate in conjunction with the shaft of the endoscope); but sleeve 15 can only move nominally in an axial direction relative to endoscope 10. Sleeve 15 is sized so that when its distal end is substantially aligned with the distal end of endoscope 10, sleeve 15 (in conjunction with base 25) will substantially cover the shaft of the endoscope. In any case, sleeve 15 is sized so that when it is mounted to endoscope 10 and endoscope 10 is inserted into a patient, sleeve 15 extends out of the body of the patient. In one preferred form of the invention, apparatus 5 is provided according to the particular endoscope with which it is intended to be used, with apparatus 5 being sized so that when base 25 is in engagement with the handle of the endoscope, the distal end of sleeve 15 will be appropriately positioned at the distal end of the endoscope, i.e., substantially aligned with the distal end of the endoscope or slightly proximal to the distal end of the endoscope.

If desired, the distal end of sleeve 15 may be provided with a radially-inwardly-extending stop (not shown) to positively engage the distal end surface of endoscope 10, whereby to prevent the distal end of sleeve 15 from moving proximally beyond the distal end surface of endoscope 10. Such a radially-inwardly-extending stop can also assist in preventing "torque slip" of sleeve 15 relative to endoscope 10 during torqueing (i.e., rotational turning) of the endoscope while within the colon, and/or "thrust slip" of sleeve 15 relative to endoscope 10 during forward pushing of the endoscope while within the colon.

Sleeve 15 preferably has a smooth outer surface so as to be non-traumatic to tissue, and is preferably made of a highly flexible material such that the sleeve will not inhibit bending of the endoscope during use. In one preferred form of the invention, sleeve 15 comprises polyurethane, polyethylene, poly(vinyl chloride) (PVC), polytetrafluoroethylene (PTFE), etc., and is preferably transparent (or at least translucent) so as to allow distance markings on endoscope 10 to be visualized through sleeve 15. And in one preferred form of the invention, sleeve 15 preferably has nominal hoop strength, so that the physician (or other operator or user) can grip endoscope 10 through sleeve 15, e.g., so as to torque the scope. If desired, sleeve 15 can include a lubricious coating (e.g., a liquid such as perfluoropolyether synthetic oil, a powder, etc.) on some or all of its interior and/or exterior surfaces, so as to facilitate disposition of the sleeve over the endoscope and/or movement of apparatus 5 through a body lumen and/or body cavity. Alternatively, sleeve 15 may be formed of a material which is itself lubricious, e.g., polytetrafluoroethylene (PTFE), etc. It should be appreciated that the inside surface of sleeve 15 may include features (e.g., ribs) to prevent the sleeve from rotating relative to the endoscope during use.

If desired, a vacuum may be "pulled" between sleeve 15 and endoscope 10, whereby to secure sleeve 15 to endoscope 10 and minimize the profile of sleeve 15. By way of example but not limitation, a vacuum may be introduced at the proximal end of sleeve 15 (i.e., at base 25) or a vacuum may be introduced at a point intermediate sleeve 15. By way of further example but not limitation, it should also be appreciated that removal of sleeve 15 from endoscope 10 (e.g., at the conclusion of a procedure) may be facilitated by introducing a fluid (e.g., air or a liquid lubricant) into the space between sleeve 15 and endoscope 10, e.g., at the proximal end of sleeve 15 (i.e., at base 25) or intermediate sleeve 15.

Still looking now at FIGS. 1-6, aft balloon 20 is secured to sleeve 15 just proximal to the articulating joint of the endoscope near to, but spaced from, the distal end of the sleeve. Aft balloon 20 is disposed concentrically about sleeve 15, and hence concentrically about an endoscope 10 disposed within sleeve 15. Thus, aft balloon 20 has a generally toroidal shape. Aft balloon 20 may be selectively inflated/deflated by means of a proximal inflation/deflation tube 45 which has its distal end in fluid communication with the interior of aft balloon 20, and which has its proximal end in fluid communication with a fitting 46 mounted to base 25. Fitting 46 is configured for connection to the aforementioned associated inflation mechanism 40. Fitting 46 is preferably a luer-activated valve, allowing inflation mechanism 40 to be disconnected from fitting 46 without losing pressure in aft balloon 20. Inflation/deflation tube 45 may be secured to the exterior surface of sleeve 15 or, more preferably, inflation/deflation tube 45 may be contained within a lumen 47 formed within sleeve 15.

Preferably aft balloon 20 is disposed a short distance back from the distal end of sleeve 15, i.e., by a distance which is approximately the same as the length of the articulating portion of a steerable endoscope 10, such that the articulating portion of the steerable endoscope will be disposed distal to aft balloon 20 when the steerable endoscope is disposed in sleeve 15. This construction allows the flexible portion of the steerable endoscope to be articulated even when aft balloon 20 has been inflated in the anatomy so as to stabilize the adjacent non-articulating portion of the endoscope relative to the anatomy, as will hereinafter be discussed in further detail. Thus, when inflated, aft balloon 20 provides a secure platform for maintaining endoscope 10 in a stable position within a body lumen or body cavity, with endoscope 10 centered within the body lumen or body cavity. As a result, endoscope 10 can provide improved visualization of the anatomy. Furthermore, inasmuch as endoscope 10 is securely maintained within the body lumen or body cavity by the inflated aft balloon 20, instruments advanced through the internal lumens (sometimes referred to as the "working channel" or "working channels") of endoscope 10 will also be provided with a secure platform for supporting those instruments within the body lumen or body cavity.

When aft balloon 20 is appropriately inflated, the aft balloon can atraumatically engage and form a sealing relationship with the side wall of a body lumen within which apparatus 5 is disposed.

In one preferred form of the invention, aft balloon 20 is formed out of polyurethane.

Base 25 is secured to the proximal end of sleeve 15. Base 25 engages endoscope 10 and helps secure the entire assembly (i.e., apparatus 5) to endoscope 10. Base 25 preferably comprises a substantially rigid or semi-rigid structure which may be gripped by the physician (or other operator or user) and pulled proximally, whereby to allow the physician (or other operator or user) to pull sleeve 15 over the distal end of endoscope 10 and then proximally back along the length of endoscope 10, whereby to mount sleeve 15 to the outer surface of the shaft of the endoscope. In one preferred form of the invention, base 25 is pulled proximally along the endoscope until base 25 seats against the handle of the endoscope, thereby prohibiting further proximal movement of base 25 (and hence thereby prohibiting further proximal movement of sleeve 15). In one preferred form of the invention, base 25 makes a sealing engagement with endoscope 10.

Push tubes 30 are slidably mounted to sleeve 15, whereby the distal ends of the push tubes can be extended and/or retracted relative to sleeve 15 (e.g., by advancing or withdrawing the push tubes via push tube handle 37, see below), and hence extended and/or retracted relative to the distal end of endoscope 10 which is disposed in sleeve 15. Preferably, push tubes 30 are slidably disposed in support tubes 50 which are secured to the outer surface of sleeve 15 or, more preferably, are contained within lumens 52 formed within sleeve 15. Support tubes 50 are preferably formed out of a low friction material (e.g., polytetrafluoroethylene, also known as "PTFE") so as to minimize resistance to movement of push tubes 30 relative to support tubes 50 (and hence minimize resistance to movement of push tubes 30 relative to sleeve 15). In this respect it should be appreciated that minimizing resistance to the movement of push tube 30 relative to support tubes 50 improves tactile feedback to the user when push tubes 30 are being used to manipulate fore balloon 35. In one form of the invention, support tubes 50 are flexible (so as to permit endoscope 10, and particularly the articulating portion of steerable endoscope 10, to flex as needed during the procedure); however, support tubes 50 also provide some column strength. Thus, when support tubes 50 are mounted within lumens 52 formed in sleeve 15, the assembly of sleeve 15 and support tubes 50 is flexible yet has a degree of column strength (whereas sleeve 15 alone is flexible but has substantially no column strength). In the event that push tubes 30 are contained within lumens 52 formed in sleeve 15, and in the event that support tubes 50 are not disposed between push tubes 30 and lumens 52, lumens 52 are preferably lubricated so as to minimize friction between push tubes 30 and lumens 52.

The proximal ends of push tubes 30 are connected to push tube handle 37. As a result of this construction, pushing distally on push tube handle 37 causes the distal ends of push tubes 30 to move distally (at the same rate) relative to sleeve 15 (whereby to move fore balloon 35 distally relative to aft balloon 20) and pulling proximally on push tube handle 37 causes the distal ends of push tubes 30 to retract proximally (at the same rate) relative to sleeve 15 (whereby to move fore balloon 35 proximally relative to aft balloon 20). Note that by moving push tubes 30 distally or proximally at the same rate, the distal ends of the push tubes are maintained parallel to each other. A clamp 53 (FIGS. 12 and 15) is provided at base 25 for holding push tubes 30 in a selected disposition relative to base 25 (and hence in a selected disposition relative to sleeve 15).

Push tubes 30 are preferably formed out of a relatively flexible material which provides good column strength, e.g., a thermoplastic polyethylene resin such as Isoplast™ (available from The Lubrizol Corporation of Wickliffe, Ohio), polyethylene, polypropylene, nylon, etc. It should be appreciated that push tubes 30 can comprise a single material or a plurality of materials, and that the stiffness of push tubes 30 can vary along their length. By way of example but not limitation, the distal-most portion of push tubes 30 can be formed of the same material as the remainder of the push tubes but have a lower modulus so as to be more flexible than the remainder of the push tubes, or the distal-most portion of push tubes 30 can comprise a different, more resilient flexible material. By way of example but not limitation, the distal-most portion of push tubes 30 can comprise Nitinol. By way of further example but not limitation, the distal-most portion of push tubes 30 can comprise a stainless steel coil covered with an outer jacket of polytetrafluoroethylene (PTFE), with the distal-most jacket/more-proximal tubing together providing a sealed lumen for inflating/deflating fore balloon 35. By forming push tubes 30 with distal ends which are more flexible than the remainder of the push tubes, the push tubes 30 and fore balloon 35 can together function as a lead (with a soft atraumatic tip) for apparatus 5 and endoscope 10, as discussed further below.

In one preferred form of the invention, push tubes 30 are configured to maintain a parallel disposition when they are in an unbiased state, i.e., when no force is being applied to push tubes 30. This is true regardless of the state of inflation or deflation of fore balloon 35.

The distal-most portion of push tubes 30 can be configured to bend inwardly or outwardly if desired. With such a configuration, when the distal tips of push tubes 30 are maintained stationary (e.g., by an inflated fore balloon, as will hereinafter be discussed) and a sufficient distally-directed force is applied to push tubes 30, the middle portions of push tubes 30 (i.e., the portions between the inflated fore balloon 35 and sleeve 15) can bend or bow outwardly, whereby to push outwardly on the side wall of the body lumen which apparatus 5 is disposed in, thereby providing a "tenting" effect on the side wall of the body lumen and/or body cavity in the space between aft balloon 20 and fore balloon 35. This "tenting" effect can significantly enhance visibility and/or tissue stability in the area distal to endoscope 10, by pushing outwardly on the side wall of the body lumen and/or body cavity in which apparatus 5 is disposed.

It should also be appreciated that by forming push tubes 30 out of a flexible material, it is possible to manually adjust their position during use (e.g., by using a separate tool, by torqueing the apparatus, etc.) so as to prevent the push tubes from interfering with visualization of the patient's anatomy and/or interfering with diagnostic or therapeutic tools introduced into the space between the fore and aft balloons. By way of example but not limitation, if apparatus 5 is disposed in the anatomy in such a way that a push tube 30 blocks visual or physical access to a target region of the anatomy, the flexible push tube 30 may be moved out of the way by using a separate tool or instrument, or by rotating the apparatus with a torqueing motion so as to move the flexible push tube 30 out of the way, etc. By way of further example but not limitation, by constructing push tubes 30 so that they are circular and flexible and of a diameter significantly smaller than the round circumference of endoscope 10, the movement of the round endoscope, when articulated, can simply push the push tubes out of the way and provides a unobstructed visual path to the tissue of interest.

It should also be appreciated that, if desired, push tubes 30 can be marked with an indicator including distance markers (not shown in the figures), e.g., colored indicators or radiopaque indicators, so that a physician (or other operator or user) observing the surgical site via endoscope 10 or by radiological guidance (e.g., X-ray fluoroscopy) can ascertain the relative disposition of push tubes 30 at the surgical site both longitudinally and/or circumferentially with respect to the side wall of the body lumen and/or other body cavity.

As will hereinafter be discussed in further detail, push tubes 30 are hollow, and have their distal ends in fluid communication with the interior of fore balloon 35 (FIGS. 1-5, 7 and 8) and their internal lumens in fluid communication with a fitting 56 mounted to base 25. Fitting 56 is configured for connection to the aforementioned associated inflation mechanism 40, in order that fore balloon 35 may be selectively inflated/deflated with air or other fluids (including liquids). Fitting 56 is preferably a luer-activated valve, allowing inflation mechanism 40 to be disconnected from fitting 56 without losing pressure in fore balloon 35.

More particularly, in one preferred form of the present invention, and looking now at FIG. 8A, push tube handle 37 comprises a hollow interior 57. Push tubes 30 are mounted to push tube handle 37 so that push tubes 30 will move in conjunction with push tube handle 37, and so that the hollow interiors of push tubes 30 are in fluid communication with the hollow interior 57 of push tube handle 37. Push tube handle 37 also comprises a fitting 58 which is in fluid communication with hollow interior 57 of push tube handle 37. A flexible tube 59 connects fitting 58 with an internal chamber (not shown) in base 25, with this internal chamber in base 25 being in fluid communication with the aforementioned fitting 56. As a result of this construction, when push tube handle 37 is moved distally, fore balloon 35 is moved distally, and when push tube handle 37 is moved proximally, fore balloon 35 is moved proximally. Furthermore, when positive fluid pressure is applied to fitting 56 in base 25, positive fluid pressure is applied to the interior of fore balloon 35, whereby to inflate fore balloon 35, and when negative fluid pressure is applied to fitting 56 in base 25, negative fluid pressure is applied to the interior of fore balloon 35, whereby to deflate fore balloon 35.

It should be appreciated that the provision of dual push tubes provides numerous advantages. By way of example but not limitation, the provision of dual push tubes provides a symmetric force to fore balloon 35 when the fore balloon is advanced distally into a body lumen, as will hereinafter be discussed. Furthermore, the provision of dual push tubes 30 provides equal outward forces against the adjacent anatomy when the push tubes are employed to straighten out the anatomy in the area proximate the distal end of endoscope 10, thereby enhancing visualization of, and/or access to, the anatomy, as will hereinafter be discussed. In addition, the provision of dual push tubes ensures that fore balloon 35 remains centered on endoscope 10, thereby facilitating un-docking of fore balloon 35 from endoscope 10 and re-docking of fore balloon 35 over endoscope 10, as will hereinafter be discussed. In addition, the provision of dual push tubes 30 helps ensure that fore balloon 35 is stable relative to the tip of the endoscope, minimizing rotational movement of the fore balloon when inflated. Furthermore, the provision of dual hollow push tubes provides a redundant air transfer system for inflating or deflating fore balloon 35.

Fore balloon 35 is secured to the distal ends of push tubes 30, whereby the spacing between aft balloon 20 and fore balloon 35 can be adjusted by moving push tubes 30 relative to sleeve 15, i.e., by moving push tube handle 37 relative to sleeve 15. Furthermore, hollow push tubes 30 provide a conduit between the interior of fore balloon 35 and fitting 56, whereby to permit selective inflation/deflation of fore balloon 35 via fitting 56.

Significantly, fore balloon 35 is configured so that (i) when it is deflated (or partially deflated) and it is in its "retracted" position relative to sleeve 15 (FIG. 2), fore balloon 35 provides an axial opening 63 (FIGS. 7, 8 and 10) sufficient to accommodate sleeve 15 and the shaft of endoscope 10 therein, whereby fore balloon 35 can be "docked" over sleeve 15 and endoscope 10, and (ii) when fore balloon 35 is in its "extended" position relative to sleeve 15 and is appropriately inflated (FIG. 4), axial opening 63 is closed down (and preferably completely closed off). At the same time, when appropriately inflated, the fore balloon can atraumatically engage and form a sealing relationship with the side wall of a body lumen and/or body cavity within which apparatus 5 is disposed. Thus, when fore balloon 35 is appropriately inflated, the fore balloon can effectively seal the body lumen and/or body cavity distal to fore balloon 35, by closing down axial opening 63 and forming a sealing relationship with the side wall of the body lumen and/or body cavity within which apparatus 5 is disposed. In this way, when push tubes 30 are advanced distally so as to separate fore balloon 35 from aft balloon 20, and when fore balloon 35 and aft balloon 20 are appropriately inflated, the two balloons will create a sealed zone therebetween (sometimes hereinafter referred to as "the therapeutic zone").

It will be appreciated that, when fore balloon 35 is reconfigured from its deflated condition to its inflated condition, fore balloon 35 expands radially inwardly (so as to close down axial opening 63) as well as radially outwardly (so as to engage the surrounding tissue).

Thus it will be seen that fore balloon 35 has a "torus" shape when deflated (to allow it to seat over the distal end of the endoscope) and a substantially "solid" shape when inflated (to allow it to close off a body lumen or body cavity).

Figure 10:
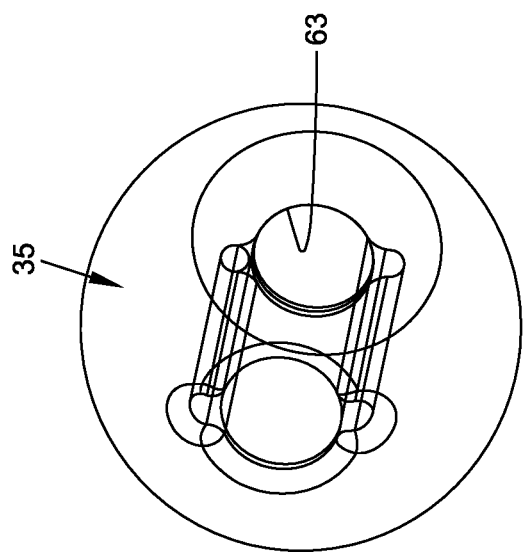
FIGS. 9 and 10 are schematic views showing construction details of the fore balloon.
Figure 9:
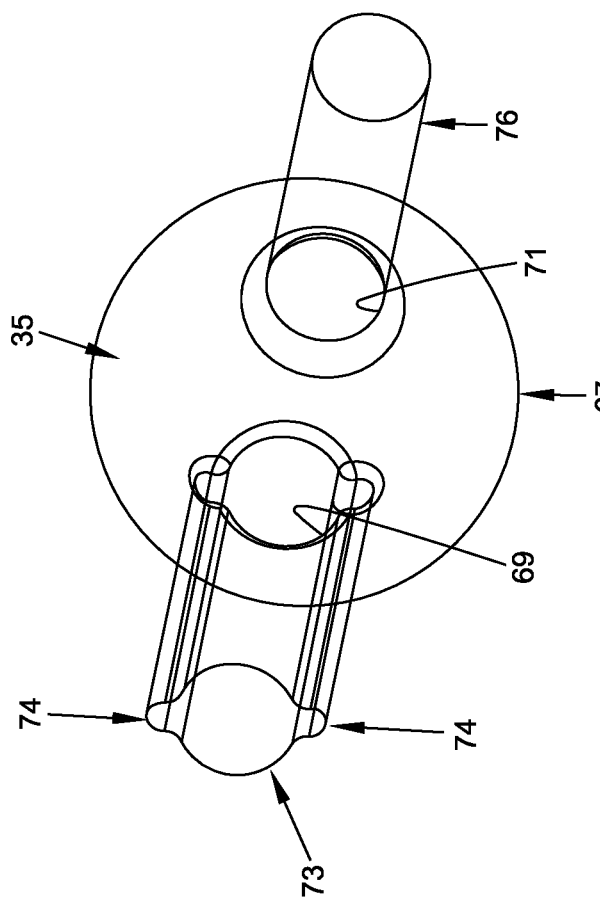

To this end, and looking now at FIGS. 9 and 10, fore balloon 35 is preferably manufactured as a single construct comprising a body 67 having a proximal opening 69 and a distal opening 71, a proximal extension 73 having a "key-shaped" cross-section comprising lobes 74, and a distal extension 76 having a circular cross-section. Note that lobes 74 are disposed on proximal extension 73 with a configuration which matches the configuration of push tubes 30 (i.e., where apparatus 5 comprises two push tubes 30 diametrically opposed to one another, proximal extension 73 will comprise two lobes 74 diametrically opposed to one another; where apparatus 5 comprises three push tubes 30 equally-circumferentially-spaced about the perimeter of sleeve 15, proximal extension 73 will comprise three lobes 74 equally-circumferentially-spaced about the perimeter of proximal extension 73; where apparatus 5 comprises one push tube 30, proximal extension 73 will comprise one lobe 74, etc.—for the purposes of the present invention, proximal extension 73 and lobe(s) 74 may be collectively referred to as having a "key-shaped" cross-section). During assembly, push tubes 30 are seated in lobes 74 of proximal extension 73, proximal extension 73 is everted into the interior of body 67 (with the interiors of hollow push tubes 30 being in fluid communication with the interior of body 67), and then distal extension 76 is everted into the interior of proximal extension 73, whereby to provide a fore balloon 35 having axial opening 63 extending therethrough, with push tubes 30 being secured to fore balloon 35 and communicating with the interior of fore balloon 35. Significantly, axial opening 63 is sized to receive the distal end of endoscope 10 therein. Also significantly, the formation of fore balloon 35 by the aforementioned process of everting proximal extension 73 into the interior of body 67, and then everting distal extension 76 into the interior of proximal extension 73, provides multiple layers of balloon material around push tubes 30, thereby providing a more robust balloon construction. Among other things, providing multiple layers of balloon material around push tubes 30 adds cushioning to the distal ends of push tubes 30, thereby providing an even more atraumatic distal tip to push tubes 30 and further ensuring that the distal tips of push tubes 30 do not damage the adjacent tissue.

In one preferred form of the invention, fore balloon 35 is formed out of polyurethane.

Figure 20:
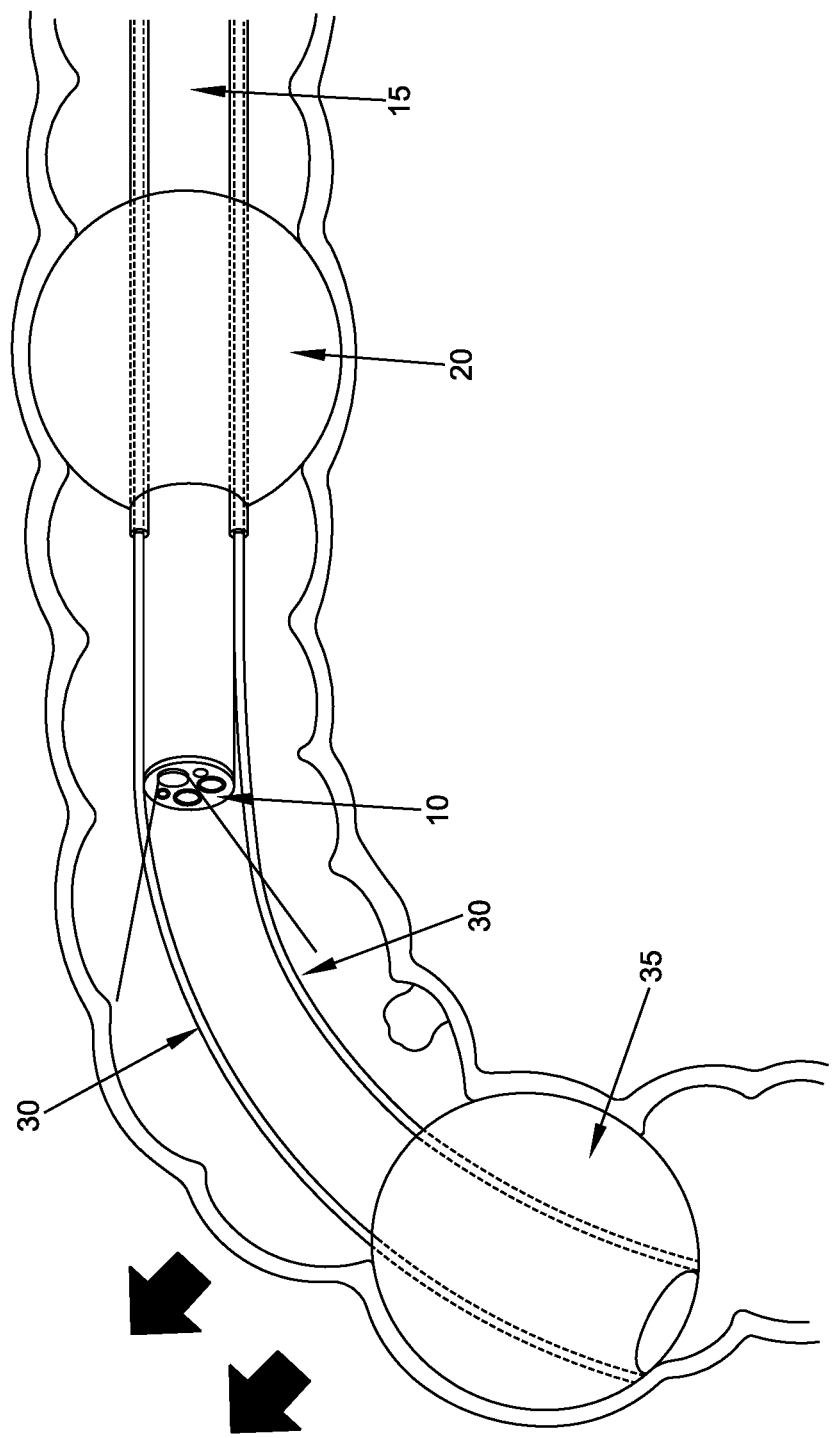

It should be appreciated that when fore balloon 35 is in its deflated condition, the material of fore balloon 35 substantially encompasses the distal ends of push tubes 30 (while still allowing push tubes 30 to be in fluid communication with the interior of fore balloon 35), thereby providing an atraumatic tip for advancing fore balloon 35 distally through a body lumen. Furthermore, push tubes 30 and the deflated fore balloon 35 can, together, essentially function as a soft-tipped lead for apparatus 5 and endoscope 10, as discussed further below (FIG. 20).

If desired, one or both of aft balloon 20 and fore balloon 35 can be marked with an indicator (e.g., a color indicator or a radiopaque indicator) so that a physician (or other operator or user) observing the surgical site via endoscope 10 or radiological guidance (e.g., X-ray fluoroscopy) can ascertain the disposition of one or both of the balloons at the surgical site.

Inflation mechanism 40 provides a means to selectively inflate aft balloon 20 and/or fore balloon 35.

Figure 11A:
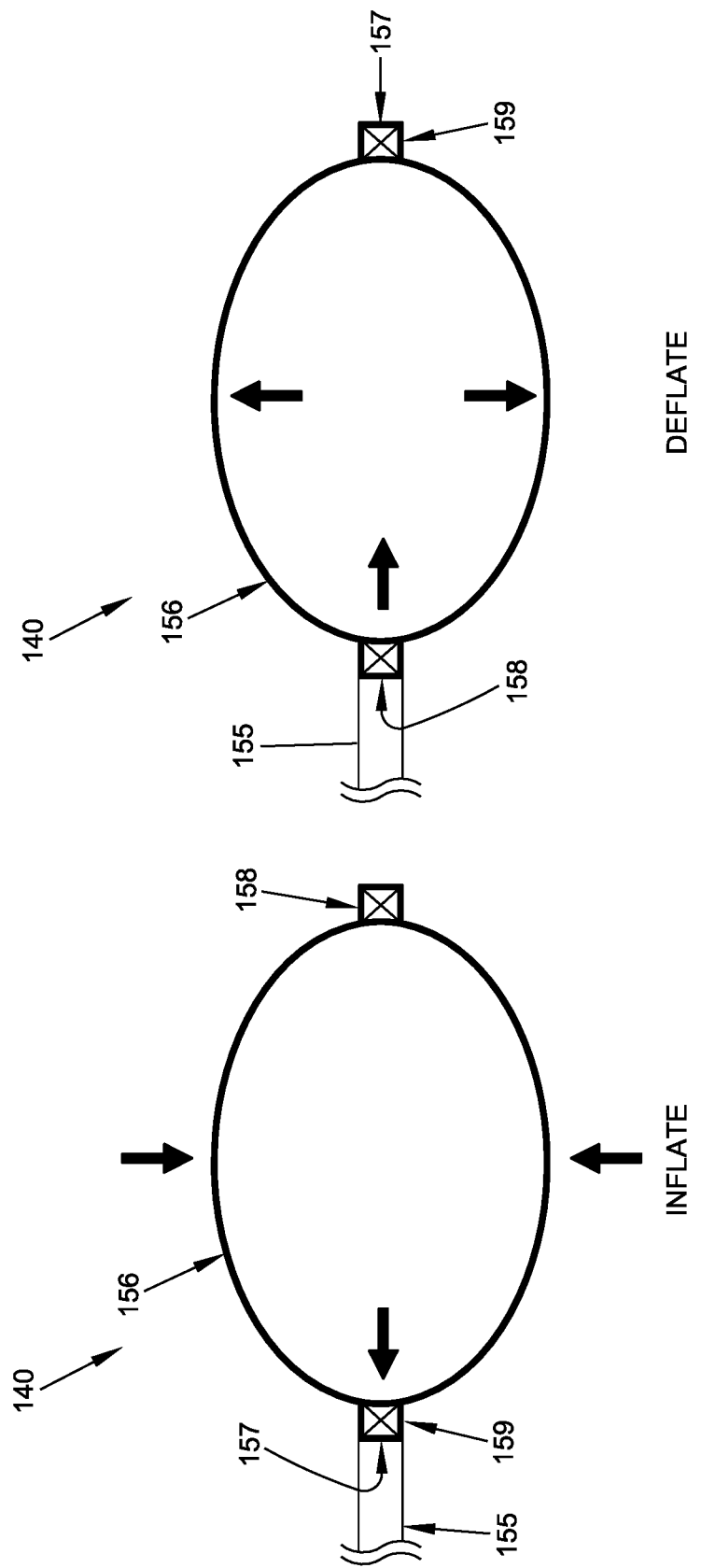
FIG. 11A is a schematic view showing another form of inflation mechanism provided in accordance with the present invention.

In one preferred form of the present invention, and looking now at FIGS. 1 and 11, inflation mechanism 40 comprises a single-line syringe inserter 140 comprising a body 145 and a plunger 150. Preferably a spring 153 is provided in body 145 to automatically return plunger 150 at the end of its stroke. Syringe inserter 140 is connected to one or the other of fittings 46, 56 via a line 155. Thus, with this construction, when single-line syringe inserter 140 is to be used to inflate aft balloon 20, syringe inserter 140 is connected to fitting 46 via line 155 so that the output of single-line syringe inserter 140 is directed to aft balloon 20 (i.e., via proximal inflation/deflation tube 45). Correspondingly, when single-line syringe inserter 140 is to be used to inflate fore balloon 35, syringe inserter 140 is connected to fitting 56 via line 155 so that the output of single-line syringe inserter 140 is directed to fore balloon 35 (i.e., via flexible tube 59 and the hollow interiors of push tubes 30).

In another preferred form of the present invention, inflation mechanism 40 comprises an elastic bulb 156 having a first port 157 and a second port 158. A one-way valve 159 (e.g., a check valve) is disposed in first port 157 so that air can only pass through first port 157 when traveling in an outward direction. Another one-way valve 159 (e.g., a check valve) is disposed in second port 158 so that air can only pass through second port 158 when traveling in an inward direction. When elastic bulb 156 is compressed (e.g., by hand), air within the interior of elastic bulb 156 is forced out first port 157; and when elastic bulb 156 is thereafter released, air is drawn back into the interior of elastic bulb 156 through second port 158.

As a result of this construction, when elastic bulb 156 is to be used to inflate aft balloon 20, first port 157 is connected to fitting 46 via line 155 so that the positive pressure output of elastic bulb 156 is directed to aft balloon 20. Elastic bulb 156 may thereafter be used to deflate aft balloon 20, i.e., by connecting second port 158 to fitting 46 via line 155 so that the suction of elastic bulb 156 is directed to aft balloon 20. Correspondingly, when elastic bulb 156 is to be used to inflate fore balloon 35, first port 157 is connected to fitting 56 via line 155 so that the positive pressure output of elastic bulb 156 is directed to fore balloon 35. Elastic bulb 156 may thereafter be used to deflate fore balloon 35, i.e., by connecting second port 158 to fitting 56 via line 155 so that the suction of elastic bulb 156 is directed to fore balloon 35.

Figure 12:
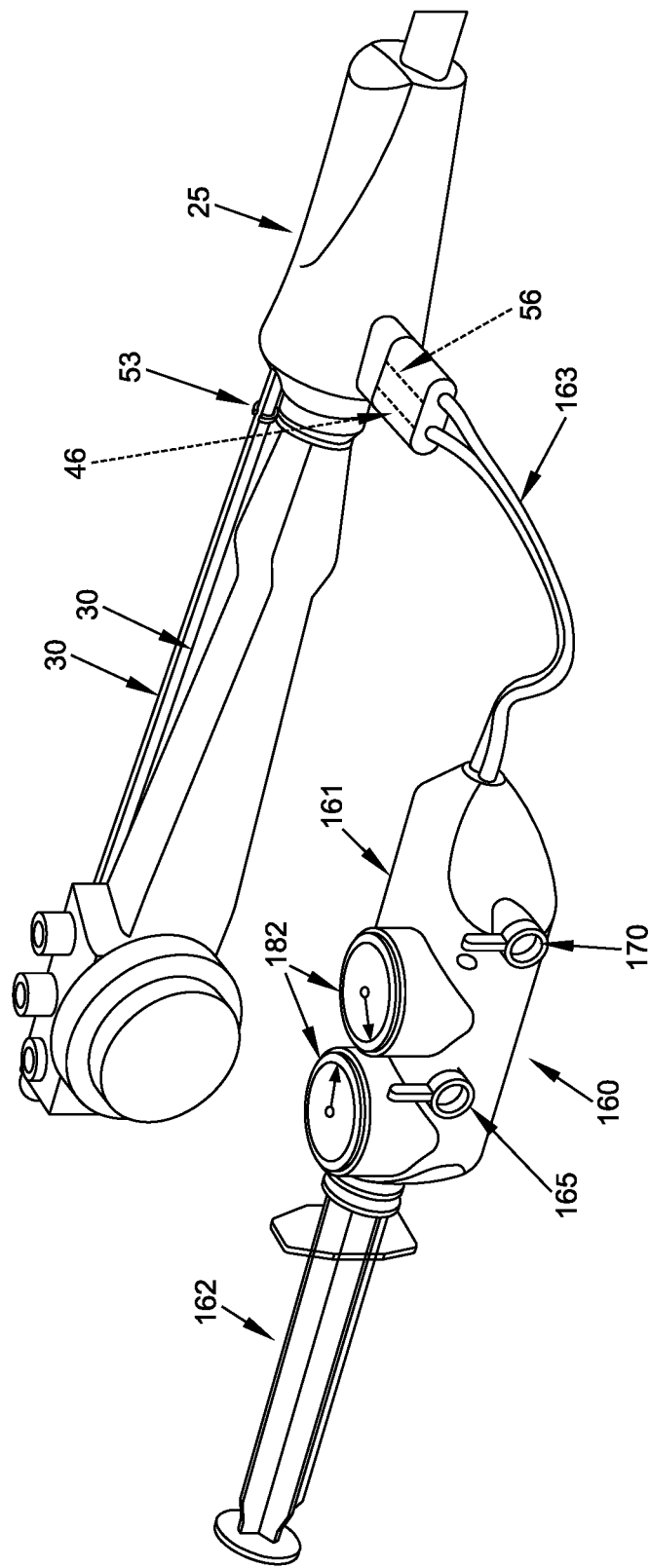
FIGS. 12 and 13 are schematic views showing another form of inflation mechanism provided in accordance with the present invention.
Figure 13:
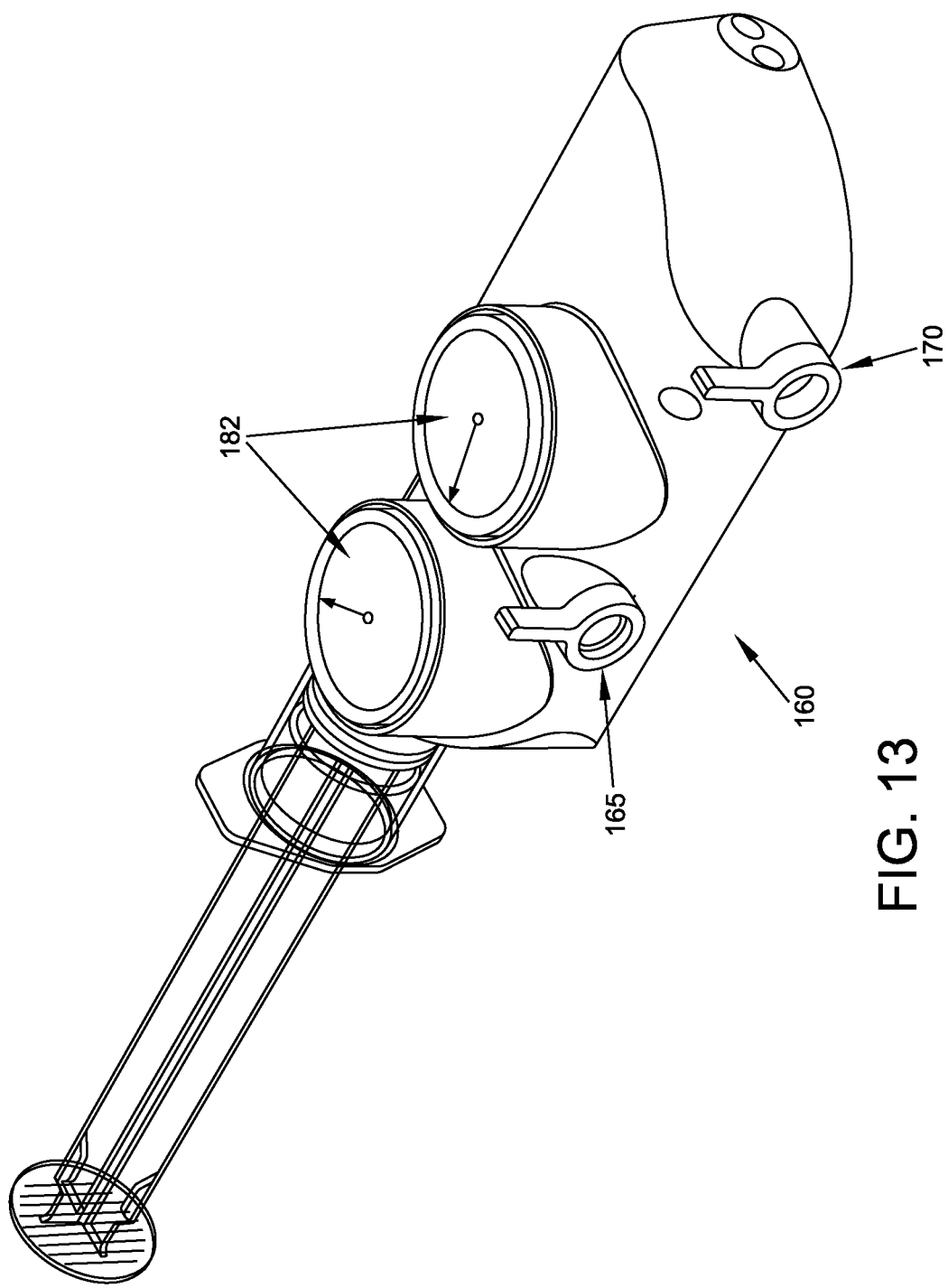

Alternatively, and looking now at FIGS. 12 and 13, a syringe 160 may be used to inflate aft balloon 20 and/or fore balloon 35. Inflation mechanism 160 comprises a body 161 and a plunger 162. Preferably a spring (not shown) is provided in body 161 to automatically return plunger 162 at the end of its power stroke. Syringe 160 is connected to fittings 46, 56 via a line 163. With this construction, syringe 160 comprises a valve 165 for connecting syringe 160 to fore balloon 35 or aft balloon 20, and a valve 170 for selecting inflation or deflation of the connected-to balloon.

Thus, with this construction, when syringe 160 is to be used to inflate aft balloon 20, valve 165 (a two-position valve that connects valve 170 to either the fore balloon or the aft balloon) is set so that the syringe 160 is connected through fitting 46 to aft balloon 20, and valve 170 (a 2-way crossover valve which allows the one-way valves to be arranged to inflate in one configuration and deflate in the other configuration) is set so that syringe 160 is providing inflation pressure. Thereafter, when aft balloon 20 is to be deflated, valve 170 is set to its deflate position.

Correspondingly, when syringe 160 is to be used to inflate fore balloon 35, valve 165 is set so that syringe 160 is connected through fitting 56 to fore balloon 35, and valve 170 is set so that syringe 160 is providing inflation pressure. Thereafter, when fore balloon 35 is to be deflated, valve 170 is set to its deflate position.

In yet another form of the invention, inflation mechanism 40 may comprise an automated source of fluid pressure (either positive or negative), e.g., an electric pump.

Figure 14:
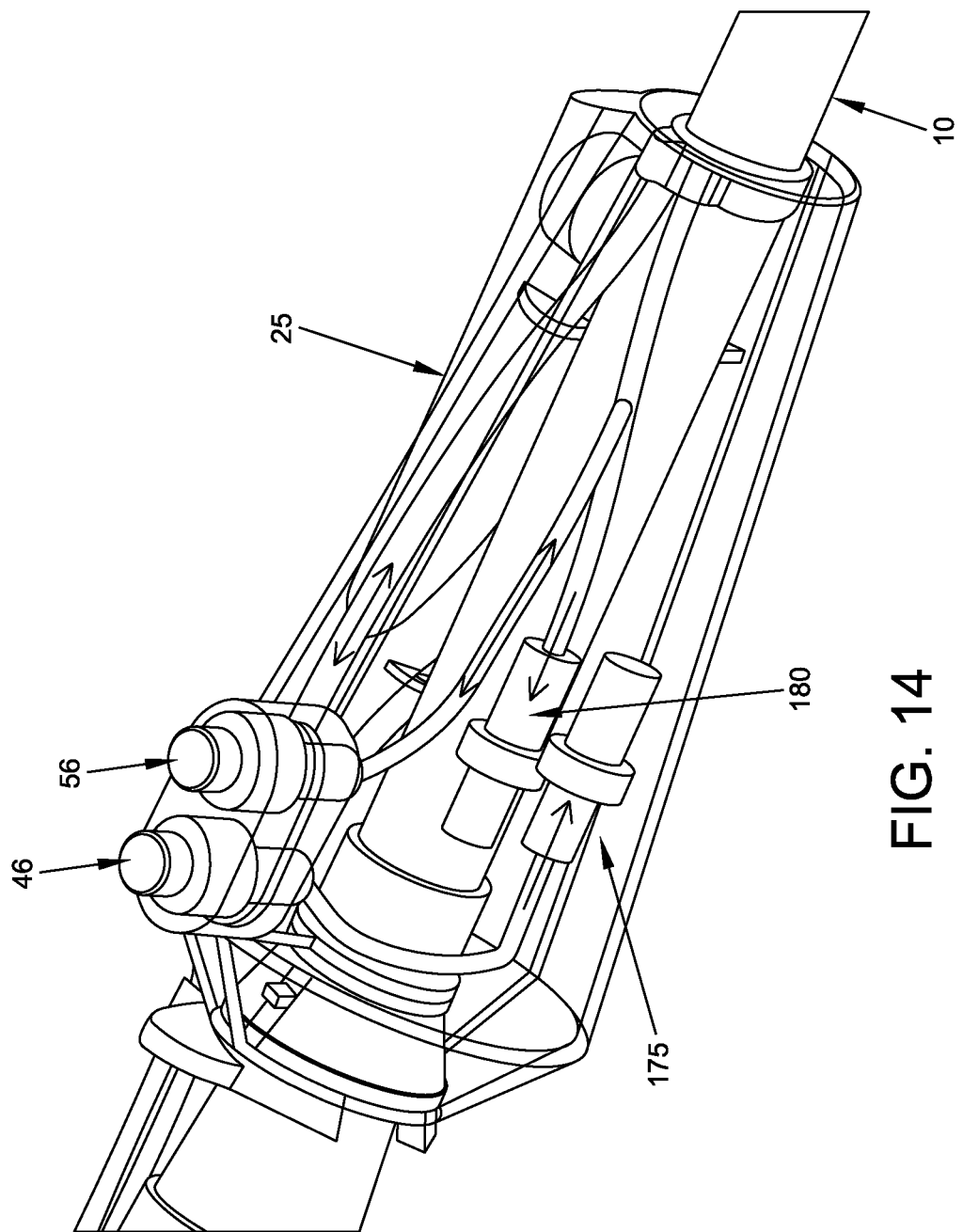
FIG. 14 is a schematic view showing relief valves which may be used to ensure that the pressure within the fore balloon and/or aft balloon does not exceed a predetermined level.

If desired, and looking now at FIG. 14, a relief valve 175 can be connected to the inflation/deflation line which connects to fore balloon 35 so as to ensure that the pressure within fore balloon 35 does not exceed a predetermined level. Similarly, and still looking now at FIG. 14, a relief valve 180 can be connected to the inflation/deflation line which connects to aft balloon 20 so as to ensure that the pressure within aft balloon 20 does not exceed a predetermined level.

Alternatively, and/or additionally, one or more pressure gauges 182 (FIG. 1 or FIG. 13) may be incorporated into the fluid line connected to aft balloon 20, and/or the fluid line connected to fore balloon 35, whereby to provide the physician (or other operator or user) with information relating to the pressure inside aft balloon 20 and/or fore balloon 35 so as to avoid over inflation and/or to help the physician (or other operator or user) ascertain the inflation state of a balloon during a procedure.

Furthermore, it will be appreciated that as fore balloon 35 moves between its "retracted" position (FIG. 2) and its "extended" position (FIG. 4), the flexible tube 59 connecting push tubes 30 to base 25 (and hence to fitting 56) may gather about base 25, potentially interfering with the physician's (or other operator's or user's) actions. Accordingly, if desired, and looking now at FIG. 15, a flexible tube retraction system 185 may be provided (e.g., within base 25) to take up slack in flexible tube 59 when fore balloon 35 is extended.

Preferred Method of Using the Novel Apparatus

Apparatus 5 may be used to manipulate, (e.g., stabilize, straighten, expand and/or flatten, etc.) the side wall of a body lumen and/or body cavity so as to better present the side wall tissue (including visualization of areas initially hidden or outside the field of view) for examination and/or treatment during an endoscopic procedure using endoscope 10, and/or to stabilize the distal tips and/or working ends of instruments (e.g., graspers, cutters or dissectors, cauterizing tools, ultrasound probes, etc.), e.g., advanced into the therapeutic zone.

More particularly, in use, sleeve 15 is first mounted to endoscope 10 (FIG. 1). This may be accomplished by pulling base 25 proximally over the distal end of endoscope 10 and then pulling proximally along the length of endoscope 10 until the distal end of sleeve 15 is substantially aligned with the distal tip of endoscope 10. At this point, aft balloon 20 is deflated, fore balloon 35 is deflated, and fore balloon 35 is docked over the distal end of endoscope 10. Endoscope 10 and apparatus 5 are ready to be inserted as a unit into the patient.

Figure 16:
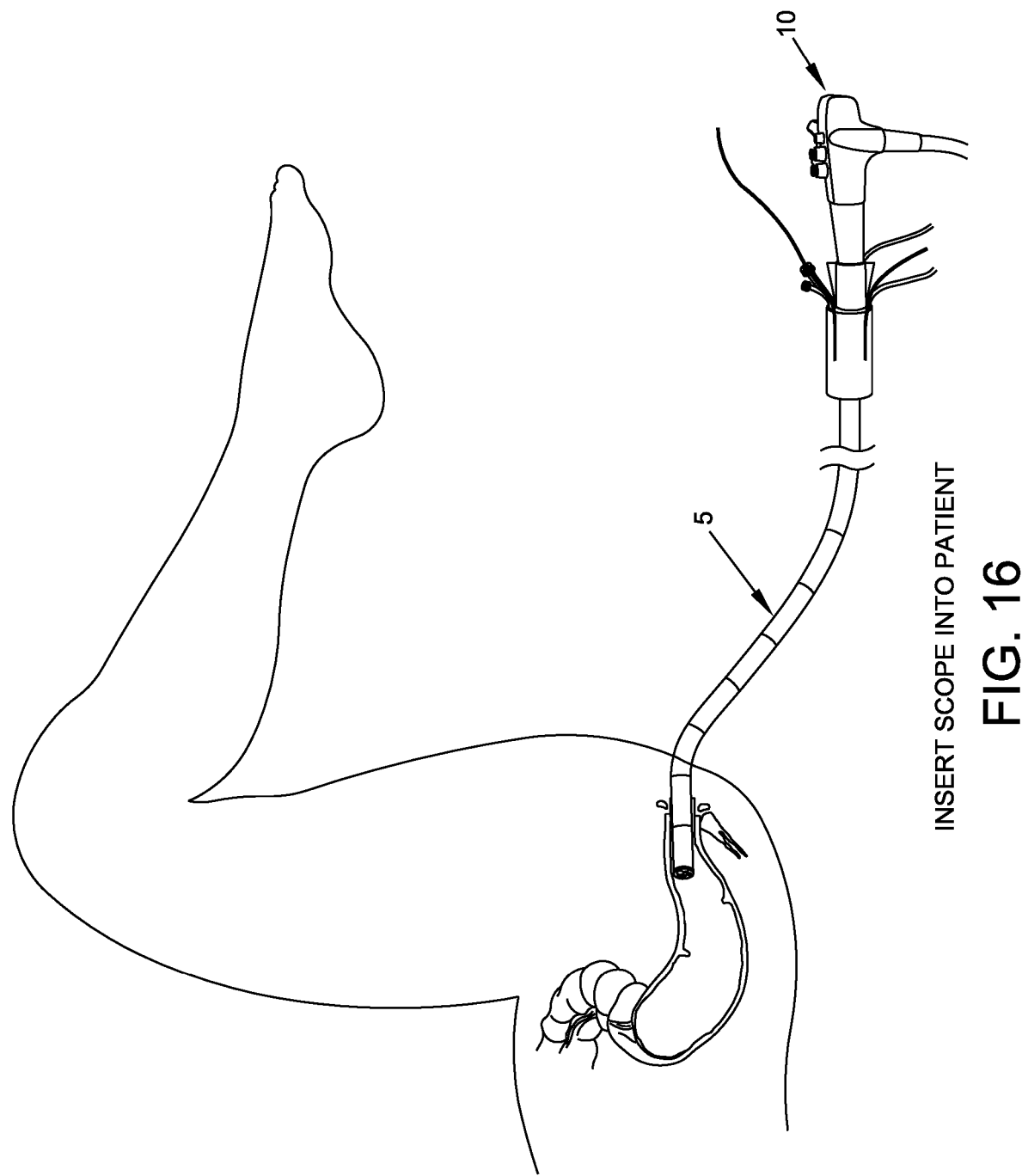
Figure 17:
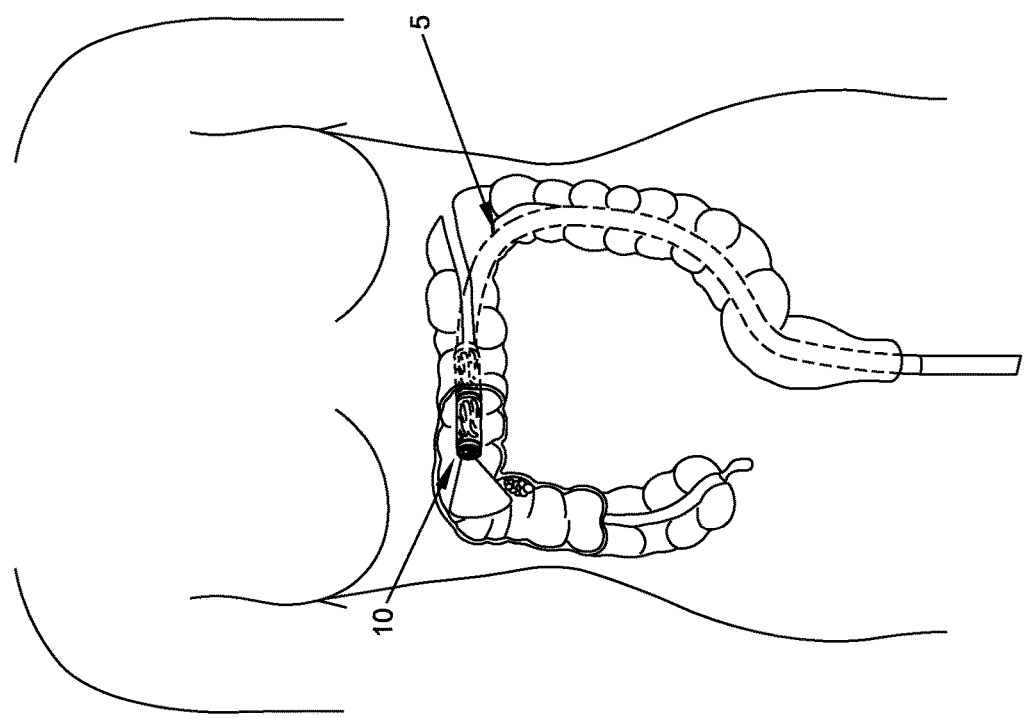
Figure 18:
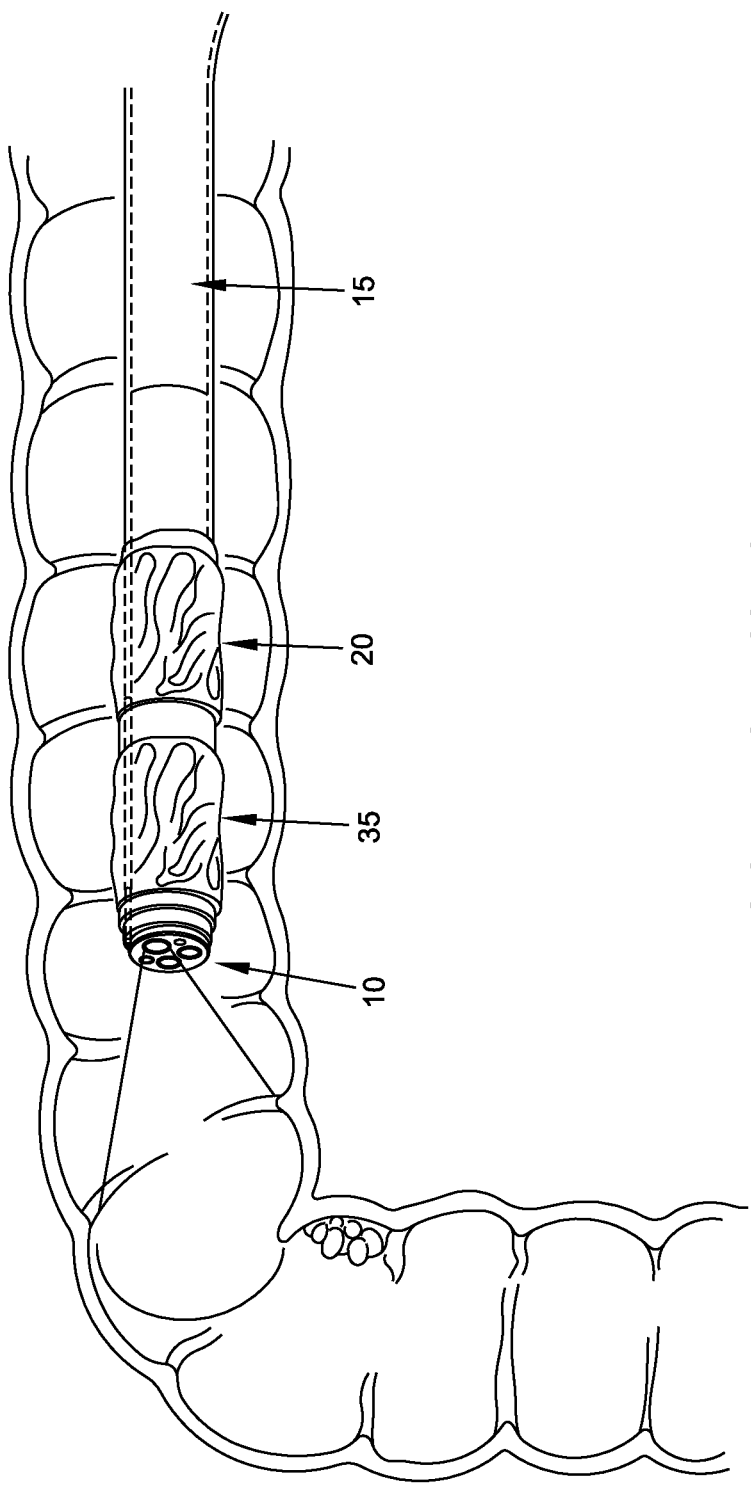

Looking next at FIG. 16, endoscope 10 and apparatus 5 are inserted as a unit into a body lumen and/or body cavity of the patient. By way of example but not limitation, endoscope 10 and apparatus 5 are inserted as a unit into the gastrointestinal (GI) tract of the patient. Endoscope 10 and apparatus 5 are advanced along the body lumen and/or body cavity to a desired location within the patient (FIGS. 17 and 18).

Figure 19:
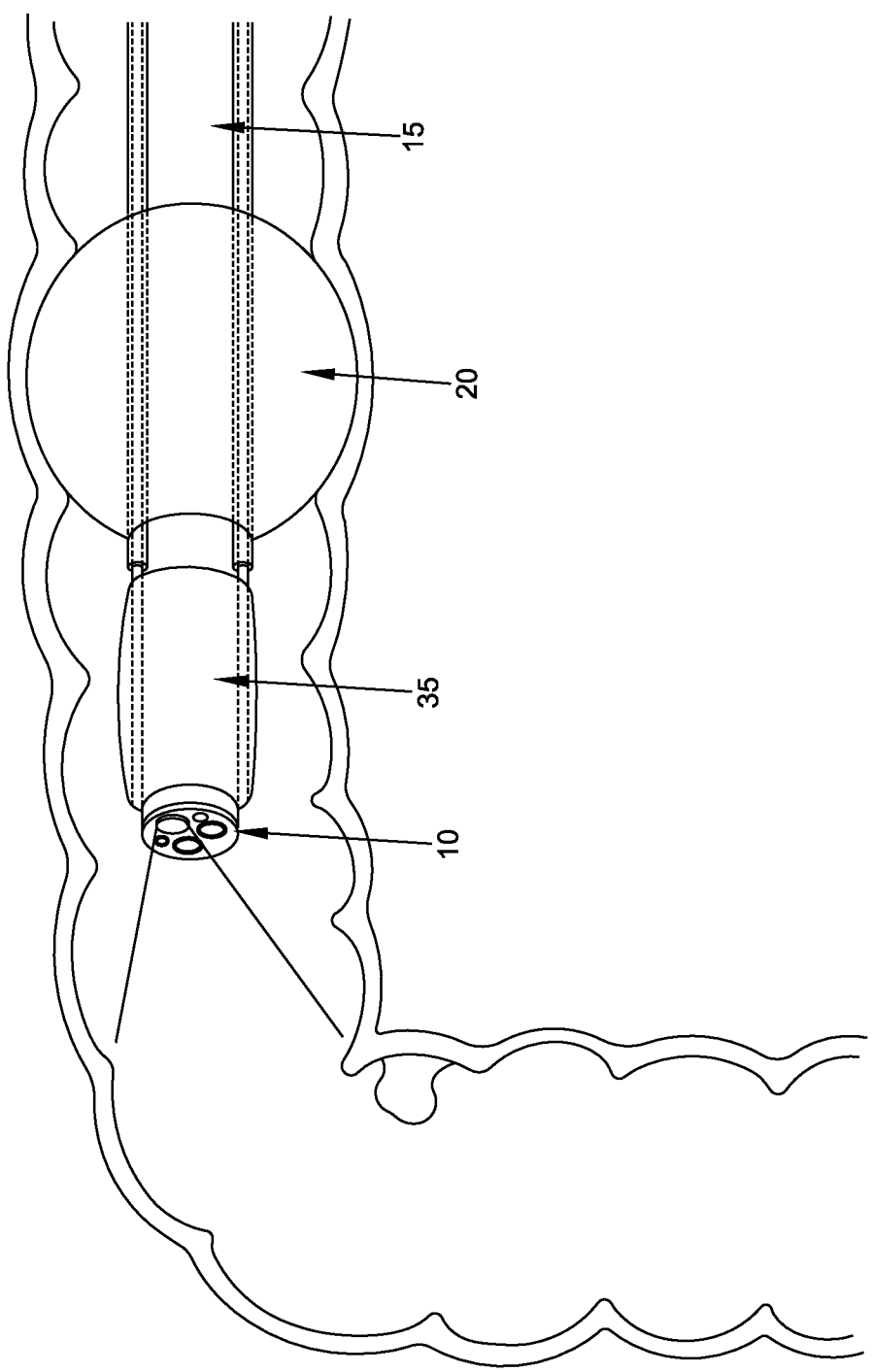

When apparatus 5 is to be used (e.g., to manipulate the side wall of the gastrointestinal tract so as to provide increased visualization of the same and/or increase access to the same, and/or for stabilizing instruments relative to the same), aft balloon 20 is inflated so as to stabilize apparatus 5 (and hence endoscope 10) within the body lumen and/or body cavity. See FIG. 19. This may be done using the aforementioned associated inflation mechanism 40.

In this respect it will be appreciated that inasmuch as the articulating portion of the endoscope resides distal to aft balloon 20, the endoscope will be able to articulate distal to aft balloon 20 so as to facilitate visualization of the anatomy even after aft balloon 20 is inflated. Significantly, such visualization is enhanced, inasmuch as aft balloon 20 stabilizes endoscope 10 within the gastrointestinal tract and distends the colon and increases the colon to a fixed diameter directly adjacent to aft balloon 20.

Next, push tubes 30 are advanced distally in the body lumen and/or body cavity (i.e., so as to move fore balloon 35 further ahead of aft balloon 20) by pushing distally on push tube handle 37. Thus, push tubes 30, and hence fore balloon 35, move distally relative to endoscope 10 (which is stabilized in position within the gastrointestinal tract by the inflated aft balloon 20). Note that the deflated fore balloon 35 covers the distal ends of push tubes 30 during such distal advancement of fore balloon 35, thereby ensuring atraumatic advancement of fore balloon 35. Note that atraumatic advancement of fore balloon 35 may be further enhanced by forming the distal ends of push tubes 30 out of a more resilient material.

When push tubes 30 have advanced fore balloon 35 to the desired position distal to endoscope 10, fore balloon 35 is inflated (FIG. 20) so as to secure fore balloon 35 to the anatomy. Again, this may be done using the aforementioned associated inflation mechanism 40. As fore balloon 35 is inflated, the inflated fore balloon 35, the inflated aft balloon 20, and push tubes 30 will all complement one another so as to stabilize, straighten, expand and/or flatten the side wall of the body lumen and/or body cavity so as to better present the side wall tissue (including visualization of areas initially hidden or outside the field of view) for examination and/or treatment during an endoscopic procedure using endoscope 10. In this respect it will be appreciated that the inflated fore balloon 35 and the inflated aft balloon 20 will together expand and tension the side wall of the body lumen and/or body cavity, and push tubes 30 will tend to straighten the anatomy between the two inflated balloons when the fore balloon is extended distally from the aft balloon. In this respect it will also be appreciated that once aft balloon 20 and fore balloon 35 have both been inflated, fore balloon 35 will create a substantially full-diameter seal across the body lumen and/or body cavity (because the inflated fore balloon closes down the axial opening 63 extending through the fore balloon when the fore balloon is in its deflated state), and aft balloon 20 will cooperate with sleeve 15 and endoscope 10 to create another substantially full-diameter barrier across the body lumen and/or body cavity. Thus, the inflated fore balloon 35 and the inflated aft balloon 20 will together define a substantially closed region along the body lumen and/or body cavity (i.e., an isolated therapeutic zone which prevents the passage of fluid and/or other liquids by virtue of the air-tight seals established by the inflated fore balloon 35 and aft balloon 20). The side wall of the body lumen and/or body cavity will be tensioned by inflation of fore balloon 35 and aft balloon 20, whereby to better present the side wall of the body lumen and/or body cavity for viewing through endoscope 10.

It should be appreciated that the expansion and tensioning of the side wall of the body lumen and/or body cavity effected by the inflated fore balloon 35, the inflated aft balloon 20, and push tubes 30, can be further enhanced by advancing the fore balloon when it is inflated and gripping the side wall of the body lumen and/or body cavity, whereby to tension the side wall of the body lumen and/or body cavity.

Significantly, inasmuch as the inflated fore balloon 35 and the inflated aft balloon 20 together define a substantially closed region along the body lumen and/or body cavity (i.e., an isolated therapeutic zone), this region can then be inflated (FIG. 21) with a fluid (e.g., air, $CO_2$, etc.) so as to further tension the side wall of the body lumen and/or body cavity, whereby to better present the side wall of the body lumen and/or body cavity for viewing through endoscope 10 and stabilize the side wall so as to facilitate more precise therapeutic interventions.

If desired, fore balloon 35 can be retracted toward aft balloon 20 (i.e., by pulling push tube handle 37 proximally), while remaining inflated (and hence maintaining a grip on the side wall of the body lumen and/or body cavity), so as to move the visible mucosa and further improve visualization and access (see FIG. 22), e.g., so as to position a particular target area on the side wall of the body lumen and/or body cavity at a convenient angle relative to the endoscope and endoscopic tools.

Alternatively, if desired, once aft balloon 35 has been inflated, push tubes 30 may be advanced distally a portion—but only a portion—of their full distal stroke, then fore balloon 35 may be inflated so as to grip the side wall of the body lumen and/or body cavity, and then push tubes 30 may be further advanced distally. This action will cause flexible push tubes 30 to bow outwardly (see FIGS. 22A-22D), contacting the side wall of the body lumen and/or body cavity and pushing the side wall of the body lumen and/or body cavity outwardly, e.g., in a "tenting" fashion, whereby to further enhance visualization of the side wall of the body lumen and/or body cavity by endoscope 10.

If desired, instruments 190 (FIG. 23) may be advanced through working channels of endoscope 10 so as to biopsy and/or treat pathologic conditions (e.g., excise pathological anatomy). It will be appreciated that such instruments will extend through the distal end of the endoscope, which is effectively stabilized relative to the anatomy via aft balloon 20, so that the working ends of instruments 190 will also be highly stabilized relative to the anatomy. This is a significant advantage over the prior art practice of advancing instruments out of the non-stabilized end of an endoscope. Preferably instruments 190 include articulating instruments having a full range of motion, whereby to better access target anatomy.

Figure 24:
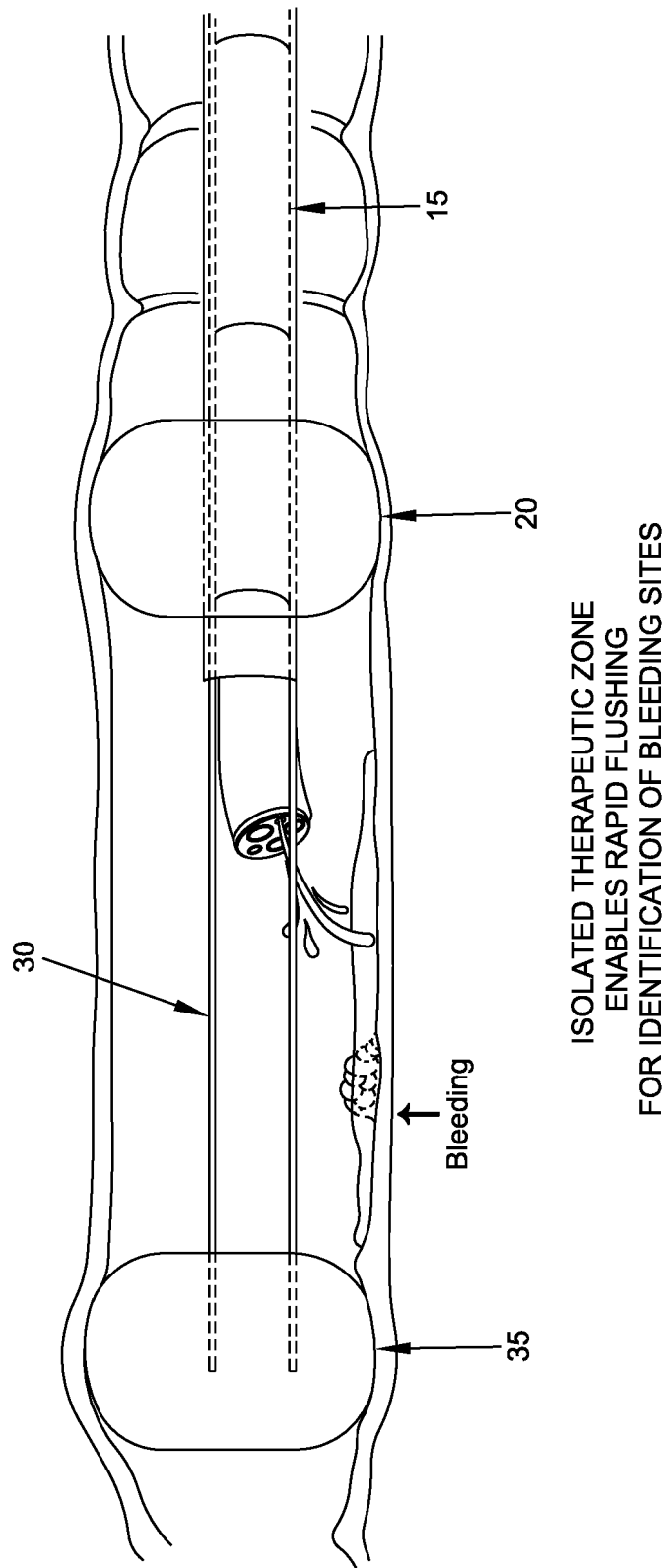
Figure 25:
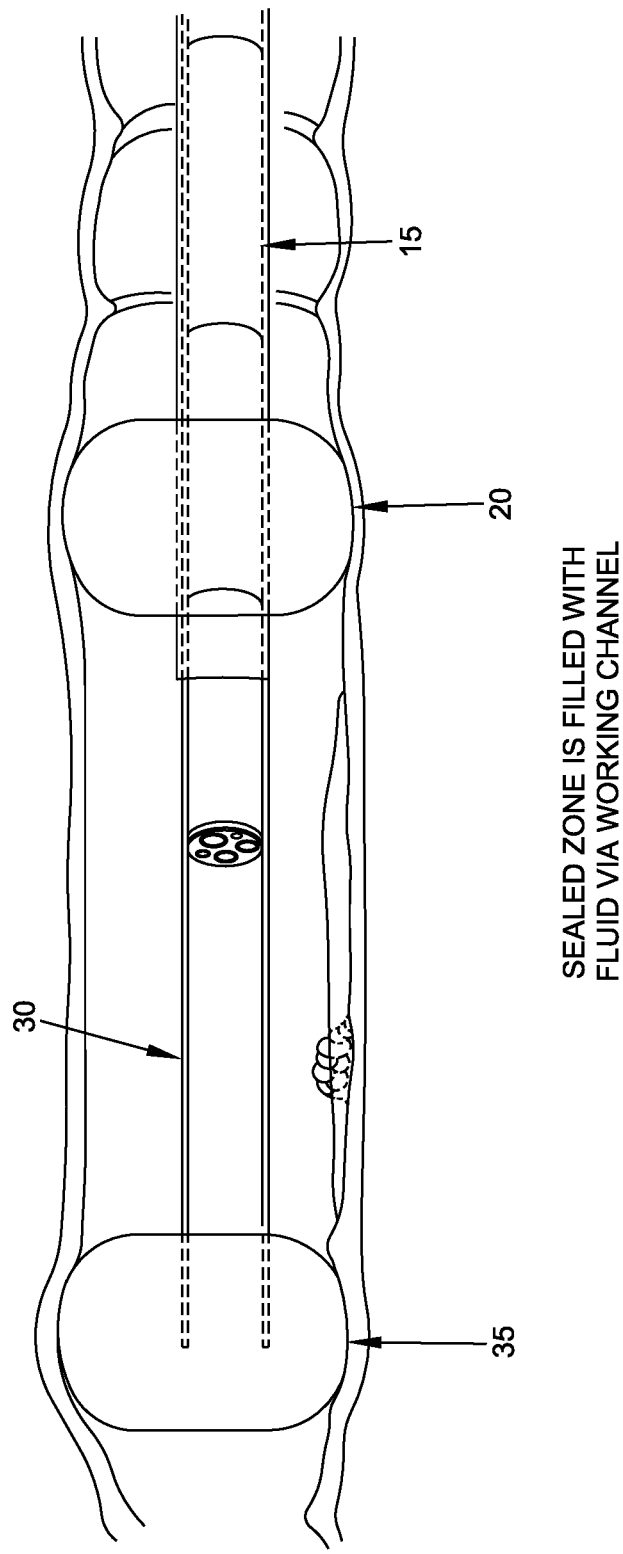
Figure 26:
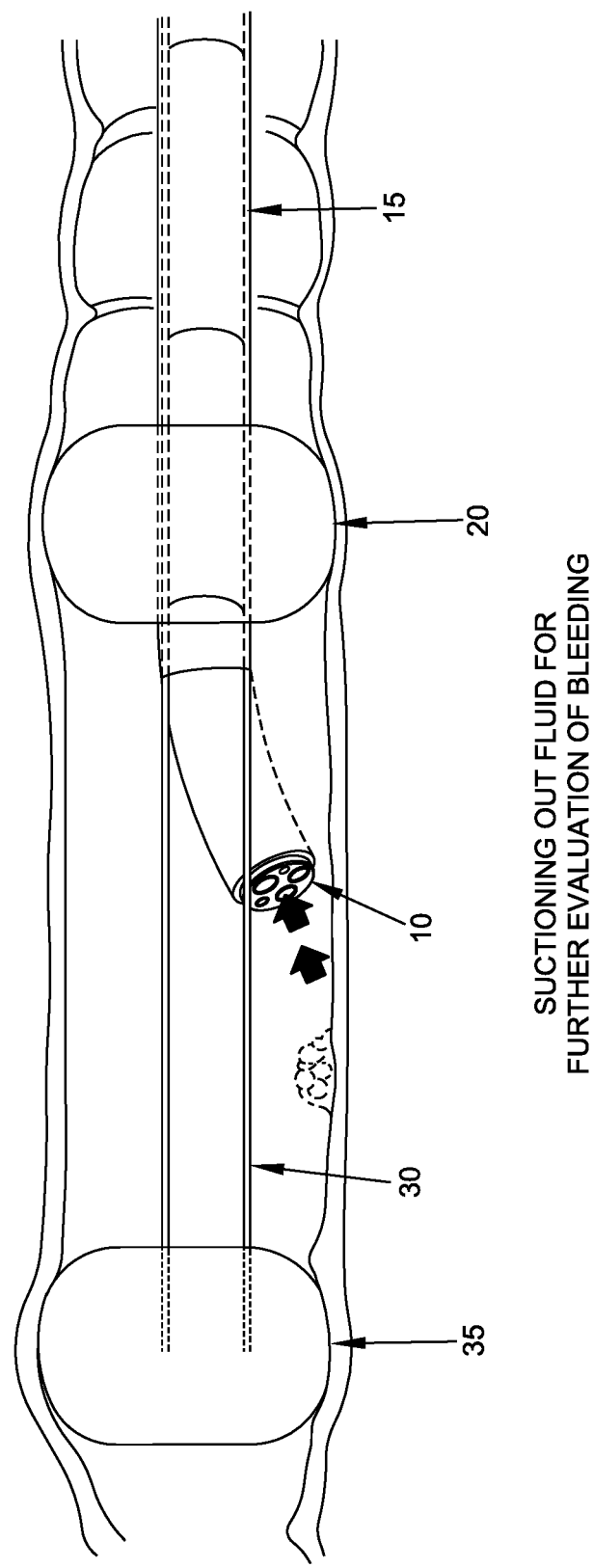

Furthermore, if bleeding were to obscure a tissue site, or if bleeding were to occur and the surgeon is unable to identify the source of the bleeding, the isolated therapeutic zone permits rapid flushing of the anatomic segment in which the therapeutic zone lies (e.g., with a liquid such as saline) with rapid subsequent removal of the flushing liquid (see FIGS. 24-26).

Figure 27:
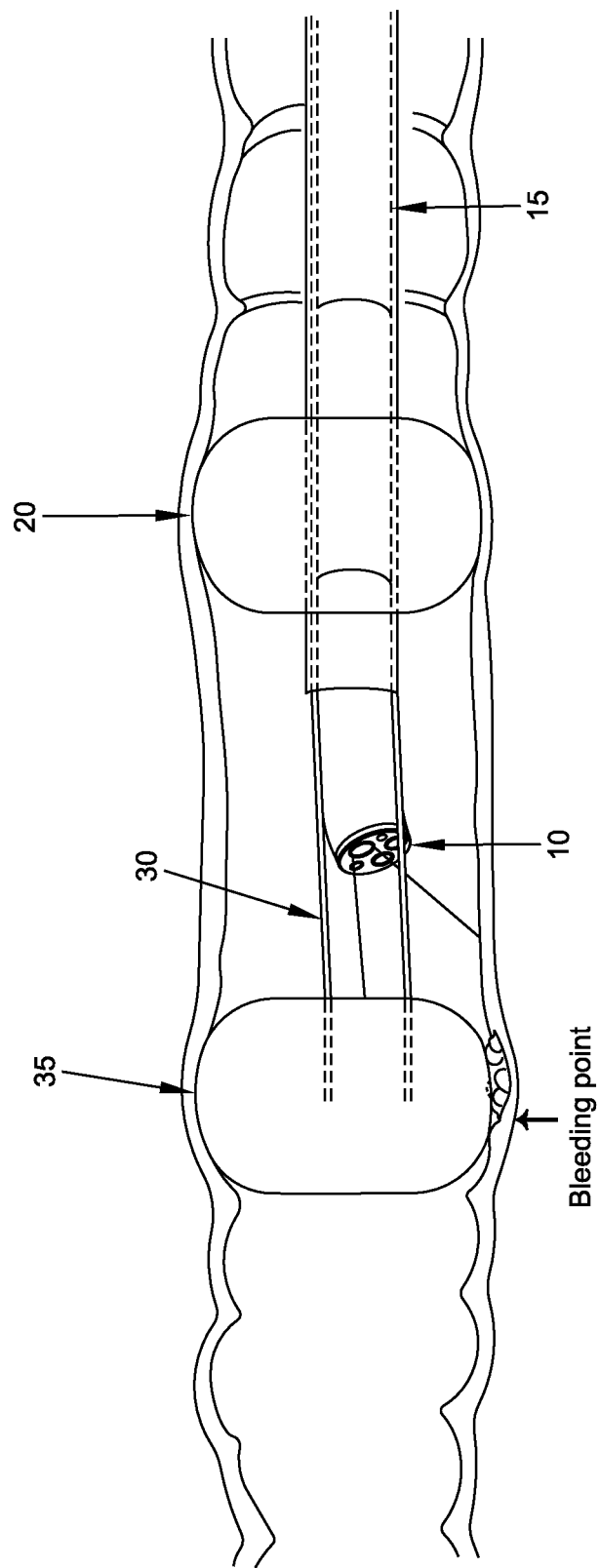

Also, if desired, fore balloon 35 can be directed with high precision to a bleeding site, whereupon fore balloon 35 may be used (e.g., inflated) to apply local pressure to the bleeding site in order to enhance bleeding control (see FIG. 27). This can be done under the visualization provided by endoscope 10.

If it is desired to reposition endoscope 10 within the anatomy with minimal interference from apparatus 5, fore balloon 35 is returned to its torus configuration (i.e., partially deflated), the fore balloon is retracted proximally and "re-docked" on the distal end of endoscope 10, aft balloon 20 is deflated, and then endoscope 10 (with apparatus 5 carried thereon) is repositioned within the anatomy. Note that where fore balloon 35 is to be re-docked on the distal end of endoscope 10, fore balloon 35 is preferably only partially deflated until fore balloon 35 is re-docked on the distal end of the endoscope, since partial inflation of fore balloon 35 can leave fore balloon 35 with enough "body" to facilitate the re-docking process. Thereafter, fore balloon 35 may be fully deflated if desired, e.g., so as to positively grip the distal end of endoscope 10.

Figure 28:
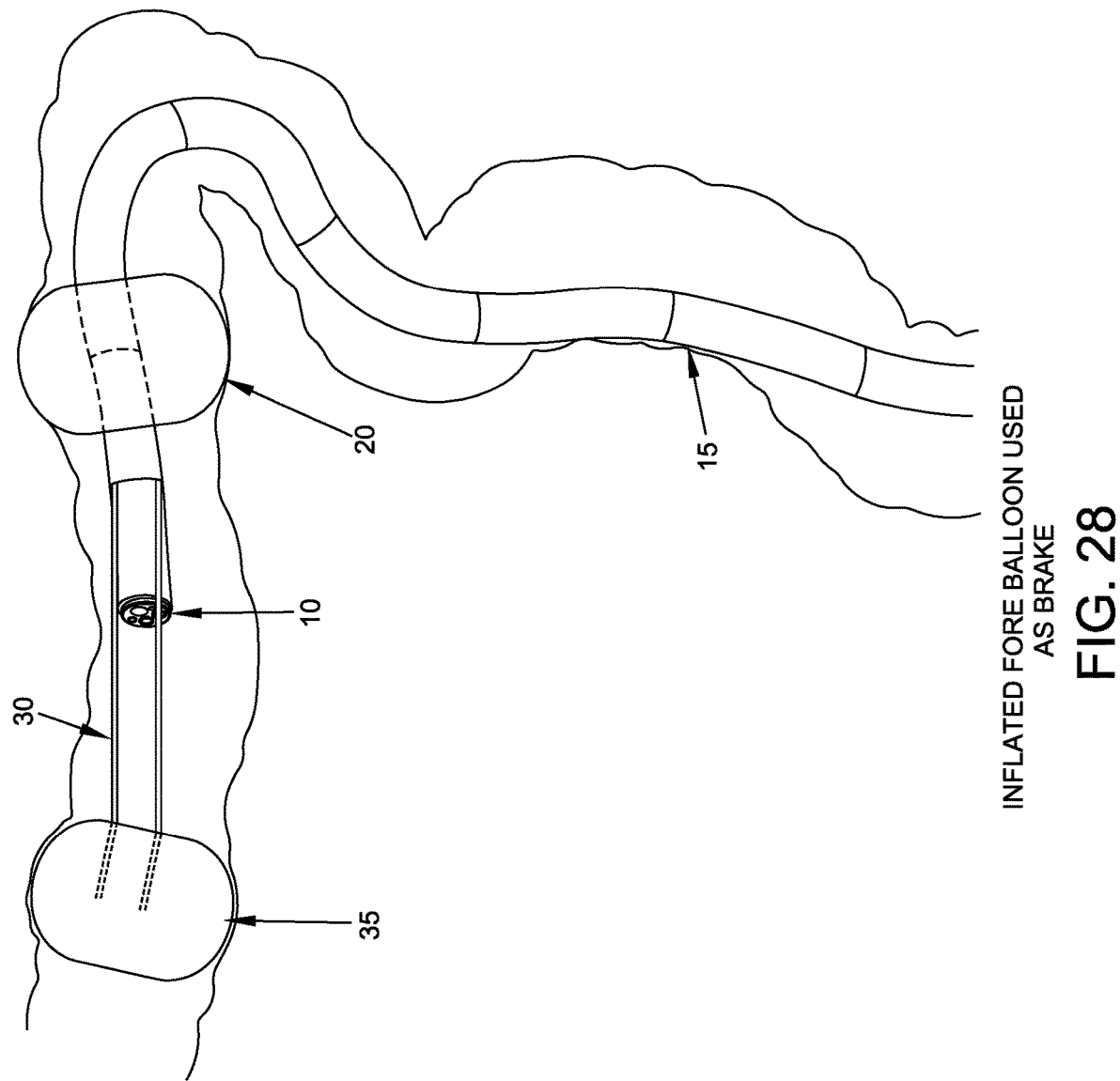
Figure 29:
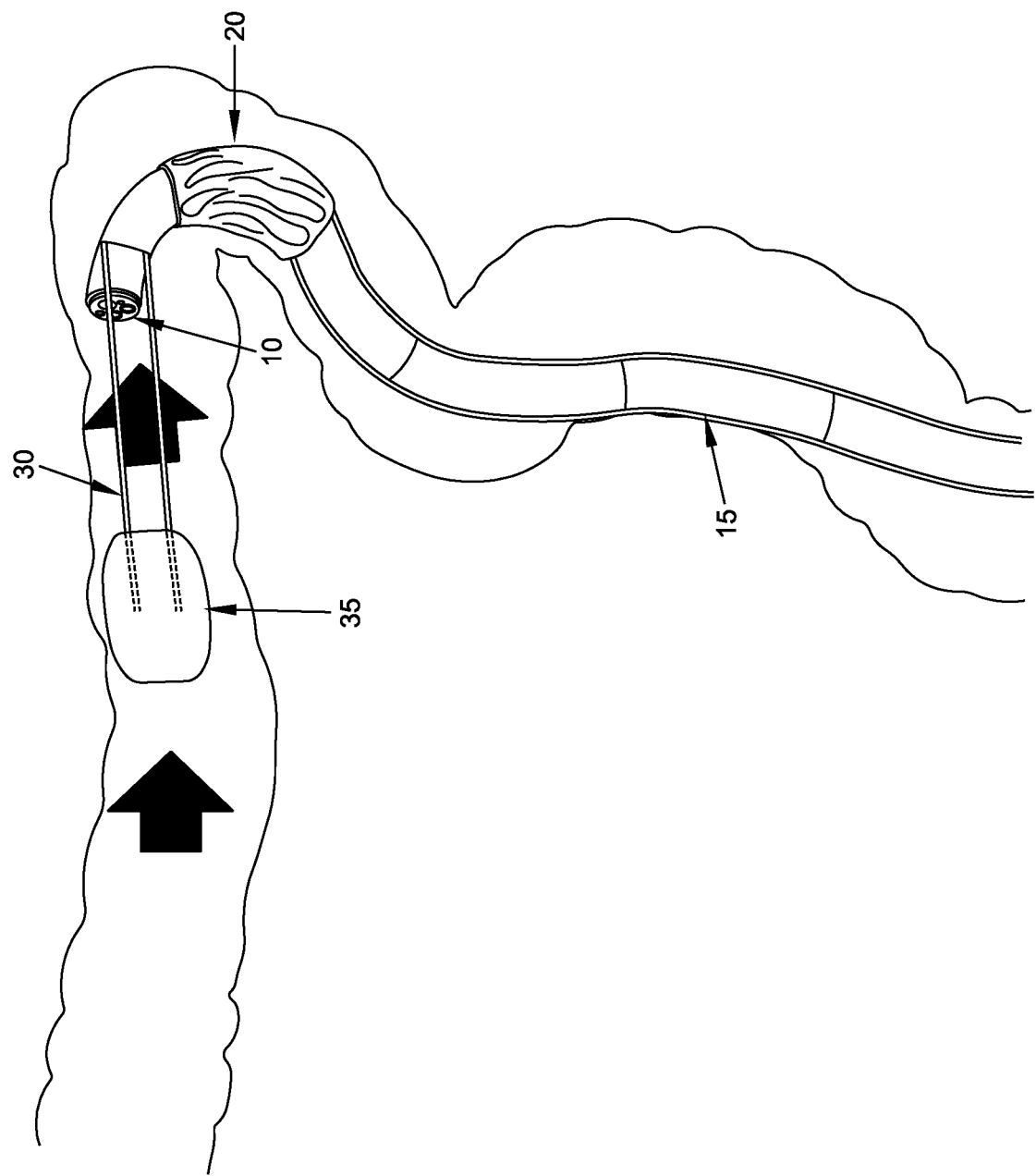
Figure 30:
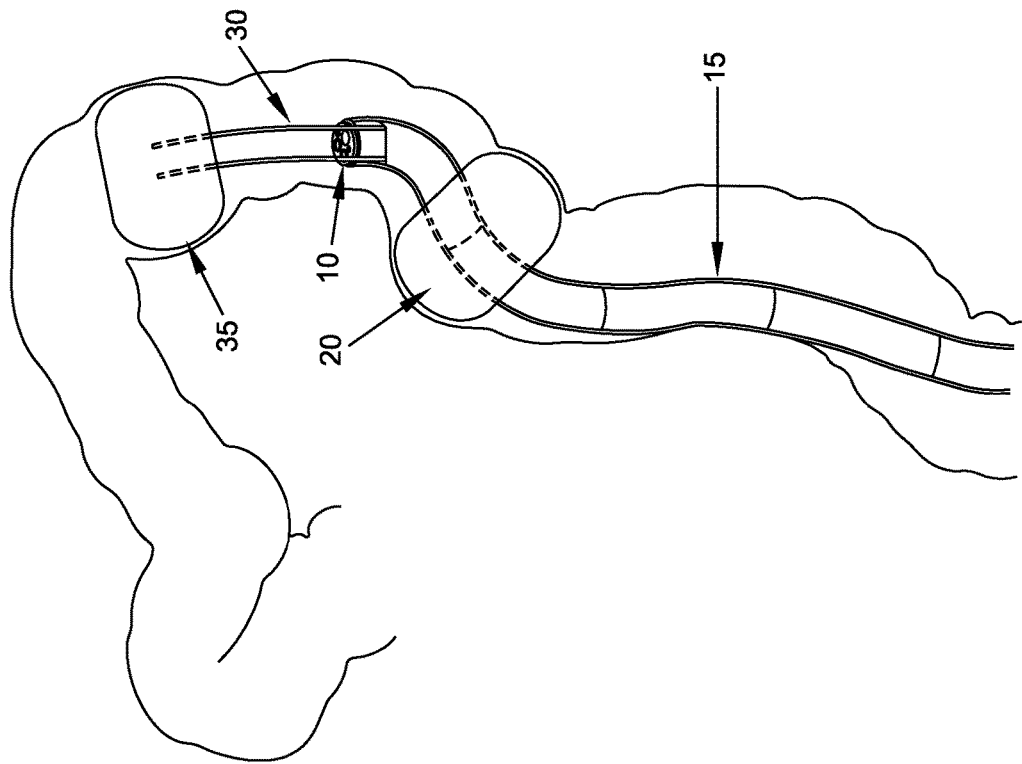

Alternatively, if desired, fore balloon 35 may be used as a drag brake to control retrograde motion of the endoscope. More particularly, in this form of the invention, endoscope 10 and apparatus 5 are first advanced as a unit into the body lumen and/or body cavity until the tip of the endoscope is at the proper location. Next, aft balloon 20 is inflated, push tubes 30 are advanced distally, and then fore balloon 35 is inflated (FIG. 28). Visualization and, optionally, therapeutic treatment may then be effected at that location. When the apparatus is to be moved retrograde, aft balloon 20 is deflated, fore balloon 35 is partially deflated, and then the endoscope is withdrawn proximally, dragging the semi-inflated fore balloon 35 along the body lumen and/or body cavity (FIG. 29), with fore balloon 35 acting as something of a brake as the endoscope is pulled proximally, thereby enabling more controlled retrograde movement of the endoscope and hence better visualization of the anatomy. If at some point it is desired, aft balloon 20 and fore balloon 35 can be re-inflated, as shown in FIG. 30, with or without introduction of a fluid into the "isolated therapeutic zone" established between the two balloons, so as to stabilize, straighten, expand and/or flatten the anatomy.

It is also possible to use aft balloon 20 as a brake when withdrawing the endoscope (and hence apparatus 5) from the anatomy, either alone or in combination with the aforementioned braking action from fore balloon 35.

At the conclusion of the procedure, endoscope 10 and apparatus 5 are withdrawn from the anatomy. Preferably this is done by deflating (or partially deflating) fore balloon 35, retracting push tubes 30 so that fore balloon 35 is "re-docked" onto the distal end of endoscope 10, fully deflating fore balloon 35 so that it grips the distal end of the endoscope, deflating aft balloon 20 (if it is not yet deflated), and then withdrawing endoscope 10 and apparatus 5 as a unit from the anatomy.

It should be appreciated that apparatus 5 may also be used advantageously in various ways other than those disclosed above. By way of example but not limitation, when endoscope 10 (and apparatus 5) is to be advanced within the colon, it may be desirable to first project fore balloon 35 distally under visual guidance of the endoscope so that fore balloon 35 leads the distal end of the endoscope. As a result, when the endoscope is advanced distally, with fore balloon 35 being deflated (or partially deflated), the fore balloon and flexible push tubes 30 may act as an atraumatic lead (guiding structure) for the endoscope as the endoscope advances through the colon. Significantly, inasmuch as the distal ends of push tubes 30 are preferably highly flexible, as the advancing fore balloon 35 encounters the colon wall (e.g., at a turn of the colon), the flexible push tubes can deflect so that the fore balloon tracks the path of the colon, thereby aiding atraumatic advancement of the endoscope along the colon. It should also be appreciated that apparatus 5 may also be used advantageously in other ways to facilitate further examinations of the luminal surface otherwise difficult to be performed currently. Such an example is endoscopic ultrasound examination of the lumen which would be facilitated by the fluid-filled inflated fore balloon and ultrasound probe examination.

Additional Constructions

If desired, apparatus 5 may be constructed so that push tubes 30 may be advanced or retracted independently of one another, as well as in conjunction with one another—such independent advancement or retraction of push tubes 30 can aid in steering the partially- or fully-deflated fore balloon 35 through the body lumen and/or body cavity, whereby to facilitate advancement or retraction of endoscope 10 through the body lumen and/or body cavity, and/or such independent advancement or retraction of push tubes 30 can facilitate applying a "turning force" to the anatomy with an inflated fore balloon 35, whereby to better present the anatomy for visualization and/or treatment.

Figure 15:
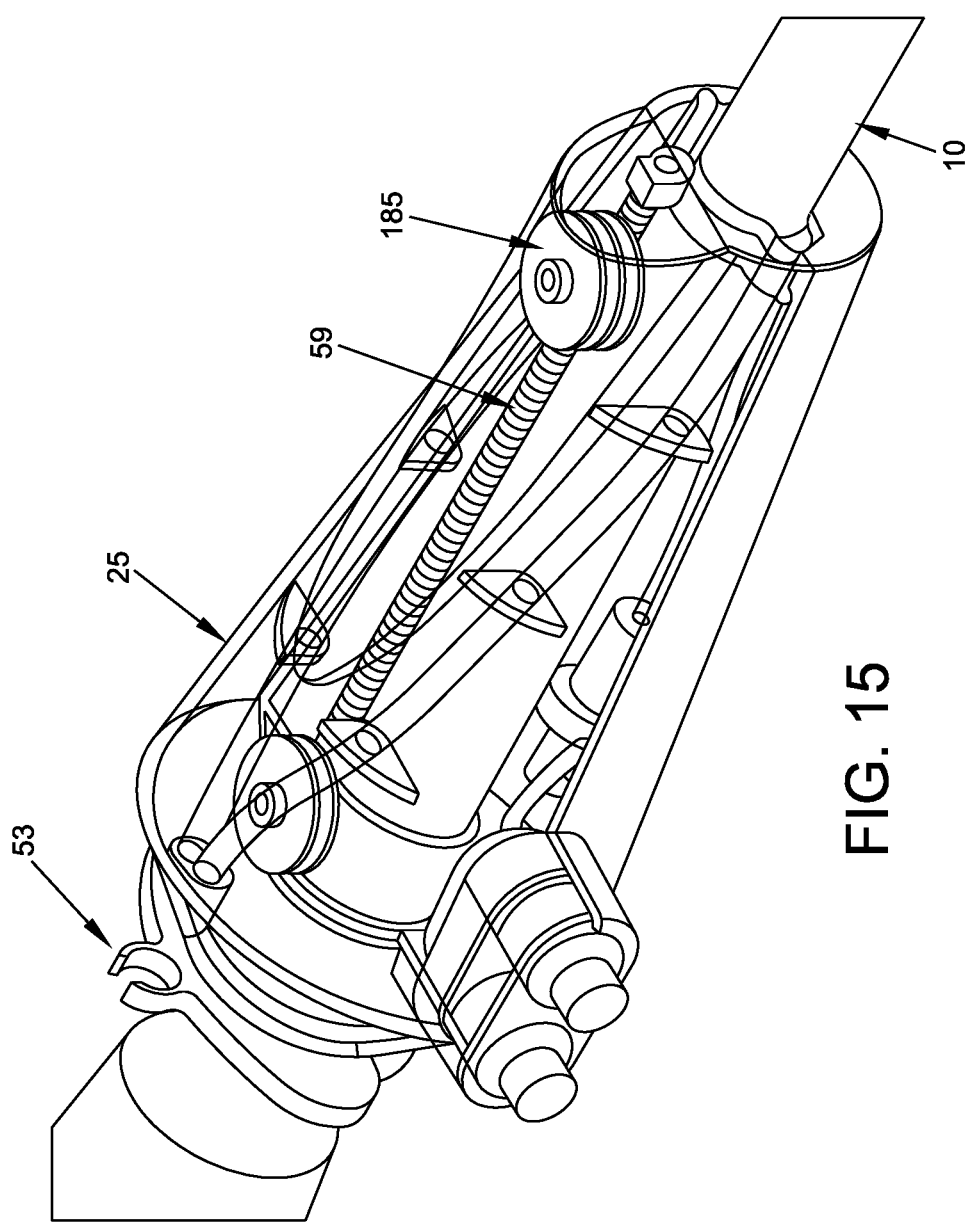
FIG. 15 is a schematic view showing a retraction system which may be used to take up slack in a flexible tube of the apparatus shown in FIG. 1.

By way of example but not limitation, in this form of the invention, and looking now at FIG. 30A, push tubes 30 are each independently slidably mounted to push tube handle 37 so that push tubes 30 can move independently of push tube handle 37 and each other. Stops 191 limit distal movement of push tubes 30 relative to push tube handle 37 so that a push tube cannot be moved completely out of push tube handle 37. As a result of this construction, when fore balloon 35 is to be moved distally, push tubes 30 are moved distally, either together or independently of one another. And when fore balloon 35 is to be moved proximally, push tubes 30 are moved proximally, either together or independently of one another. At any point in a procedure, push tubes 30 can be moved independently of one another so as to "turn" the fore balloon, e.g., such as when fore balloon 35 is inflated and engaging the anatomy, whereby to apply a "turning force" to the anatomy, or where fore balloon 35 is partially inflated and is being used as an atraumatic tip for the advancing assembly, whereby to help "steer" the assembly through the anatomy. Note that it may be desirable to provide a limiting mechanism to limit the extent to which push rods 30 may be moved, longitudinally, independently of one another, in order to prevent excessive turning of fore balloon 35, and/or push rod cross-over, and/or push rod entanglement, and/or push rod misalignment, etc. Note also that push tubes 30 may be held in a particular disposition by mounting push tubes 30 in the aforementioned clamp 53 (FIGS. 12 and 15).

It should also be appreciated that it is possible to modify the construction of sleeve 15 so as to support instruments (or hollow instrument guide tubes) external to endoscope 10. More particularly, looking again at FIGS. 5 and 6, it will be seen that in the construction shown in FIGS. 5 and 6, sleeve 15 comprises a lumen 47 for receiving inflation/deflation tube 45 for inflating/deflating aft balloon 20, and a pair of lumens 52 for receiving support tubes 50 which receive push tubes 30 for manipulating and inflating/deflating fore balloon 35. However, if desired, sleeve 15 may include additional lumens for supporting instruments (or hollow instrument guide tubes) external to endoscope 10.

Figure 31:
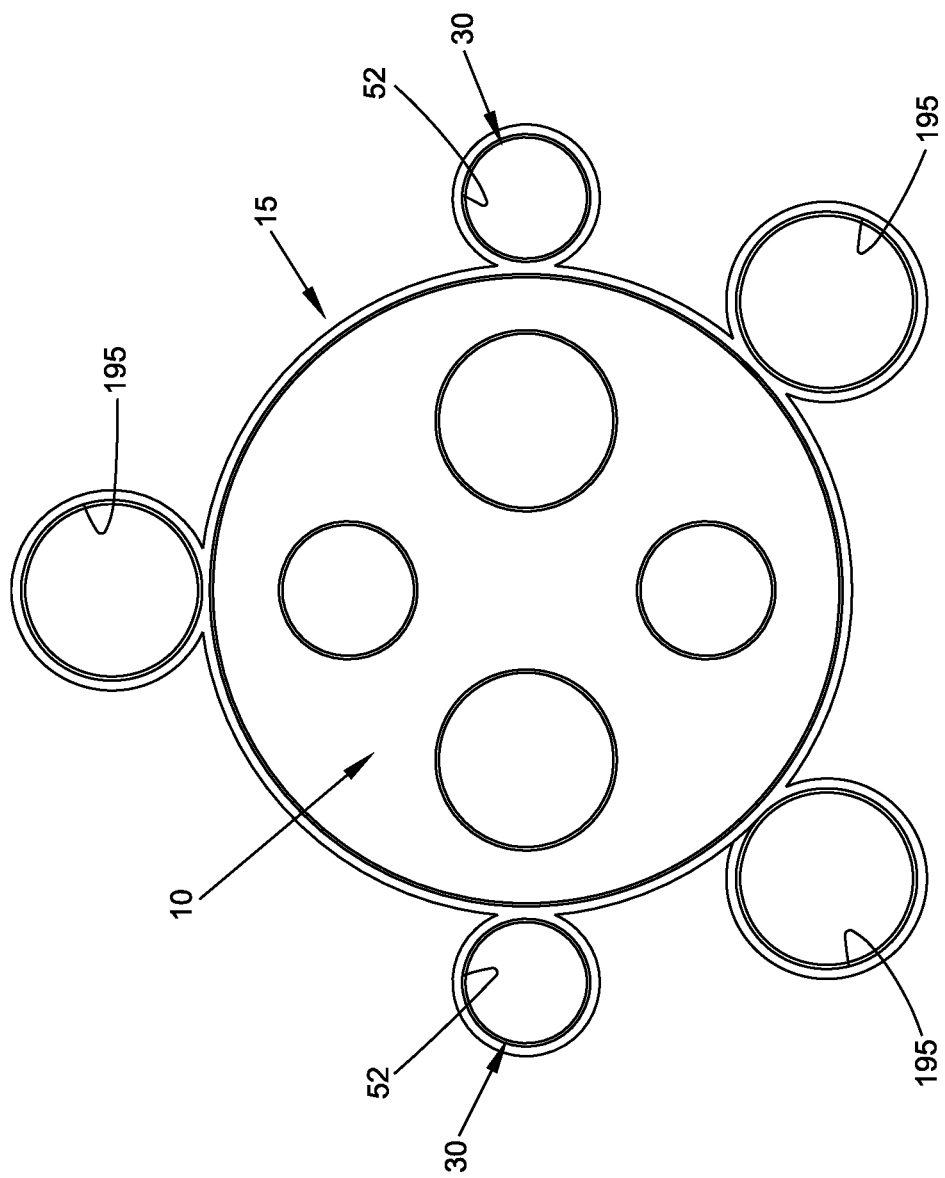
FIG. 31 is a schematic view showing another form of the sleeve, wherein the sleeve comprises additional lumens for receiving instruments.
Figure 32:
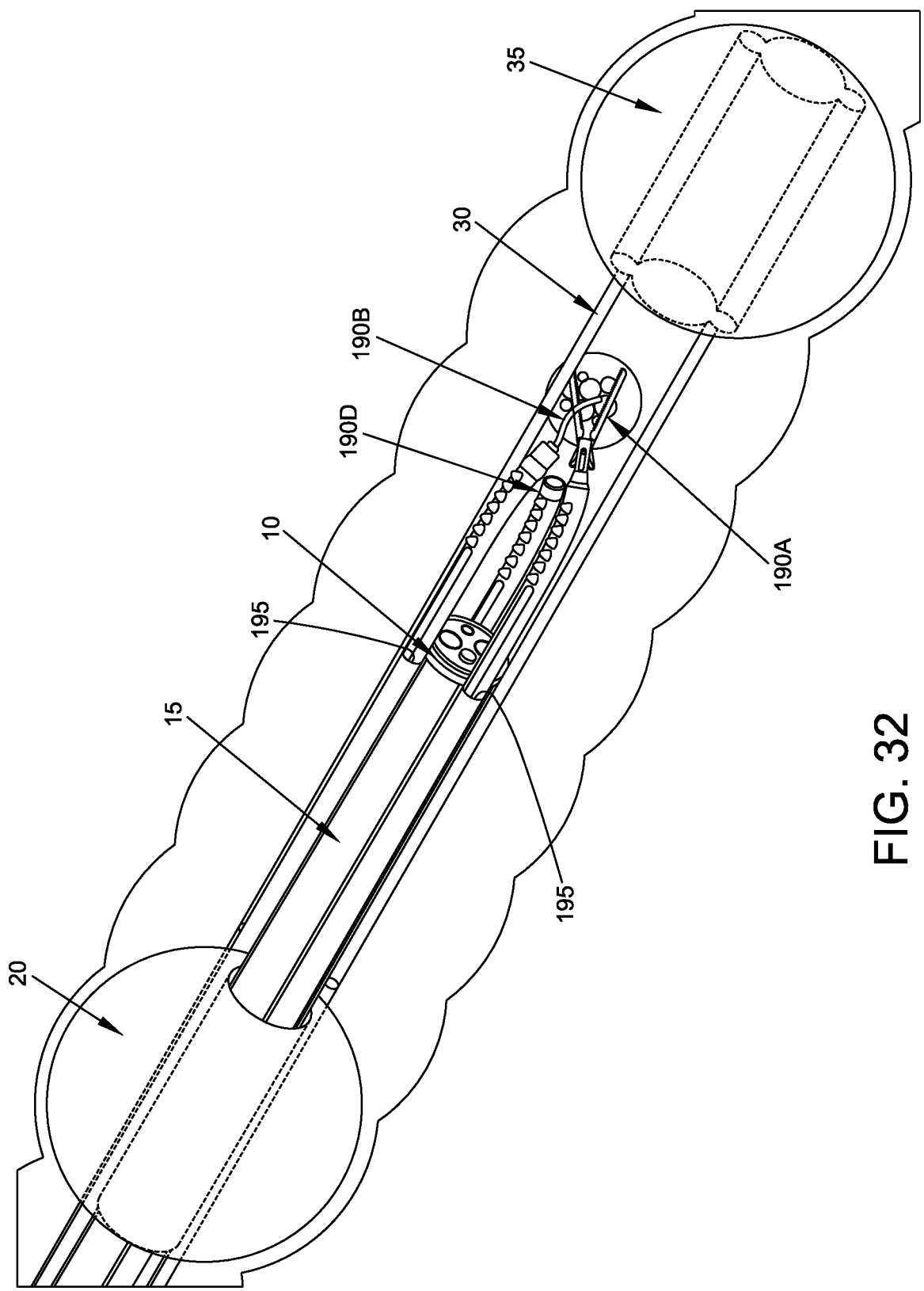
FIGS. 32-35 are schematic views showing how instruments may be advanced through the additional lumens of the sleeve.
Figure 33:
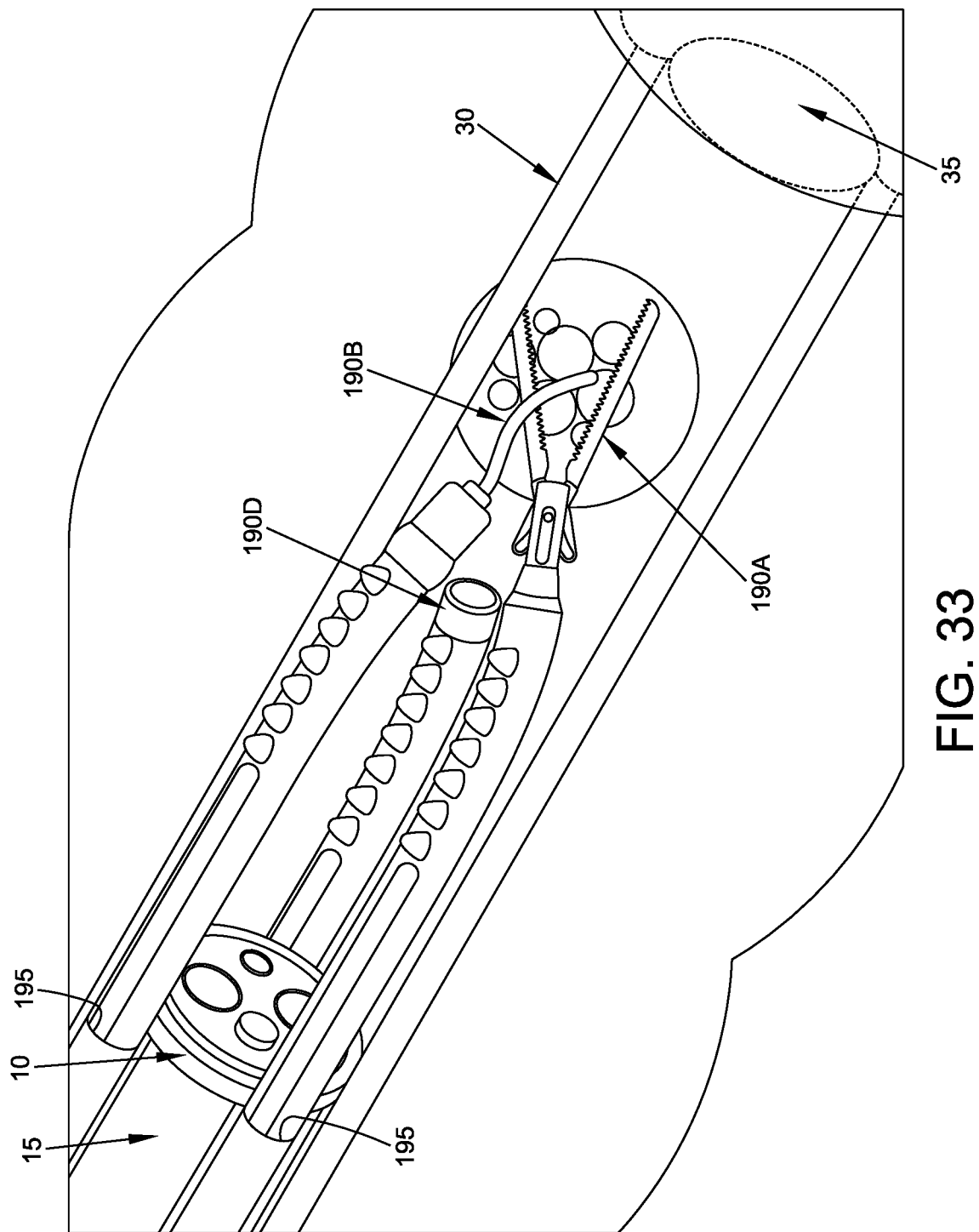
Figure 34:
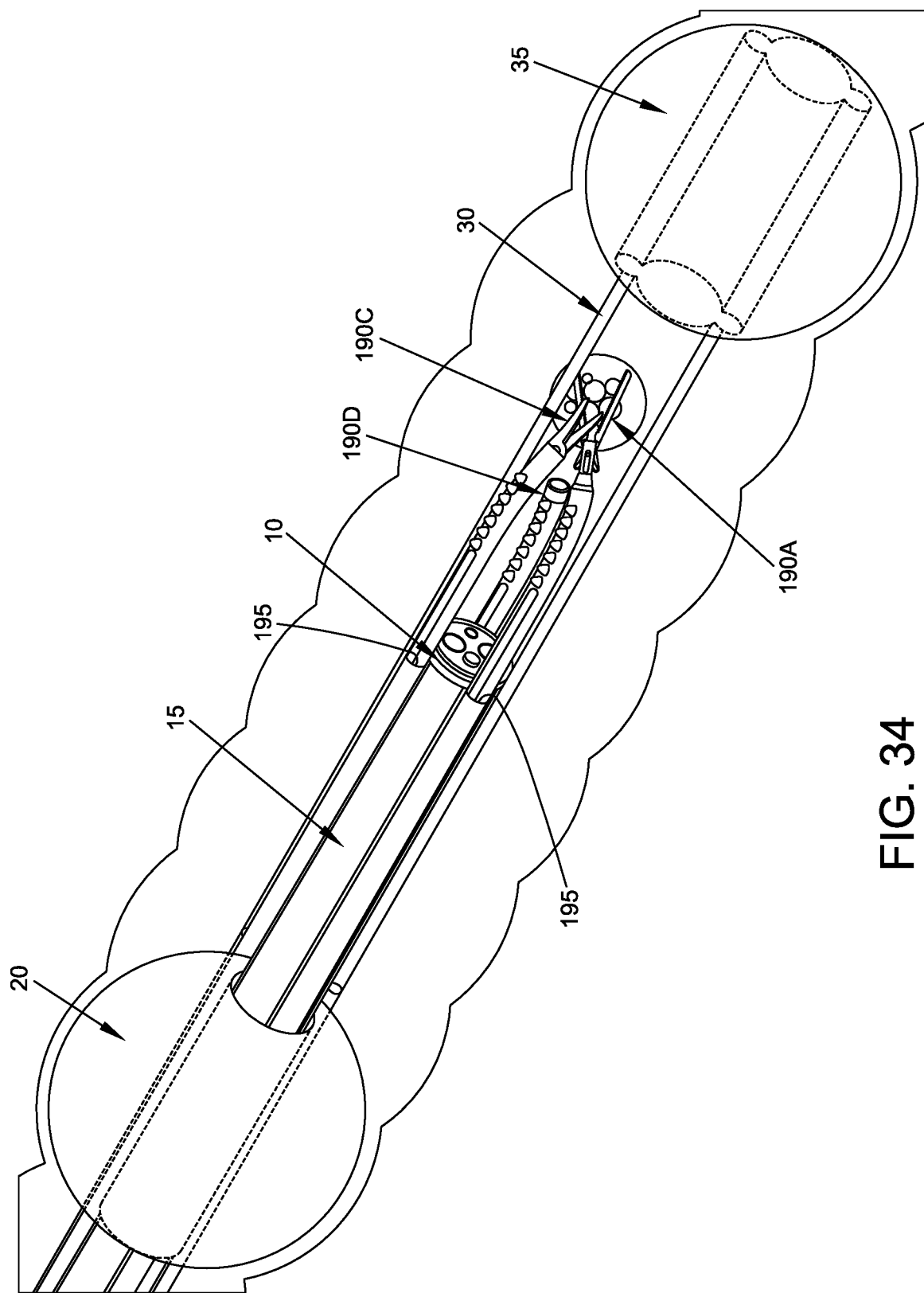
Figure 35:
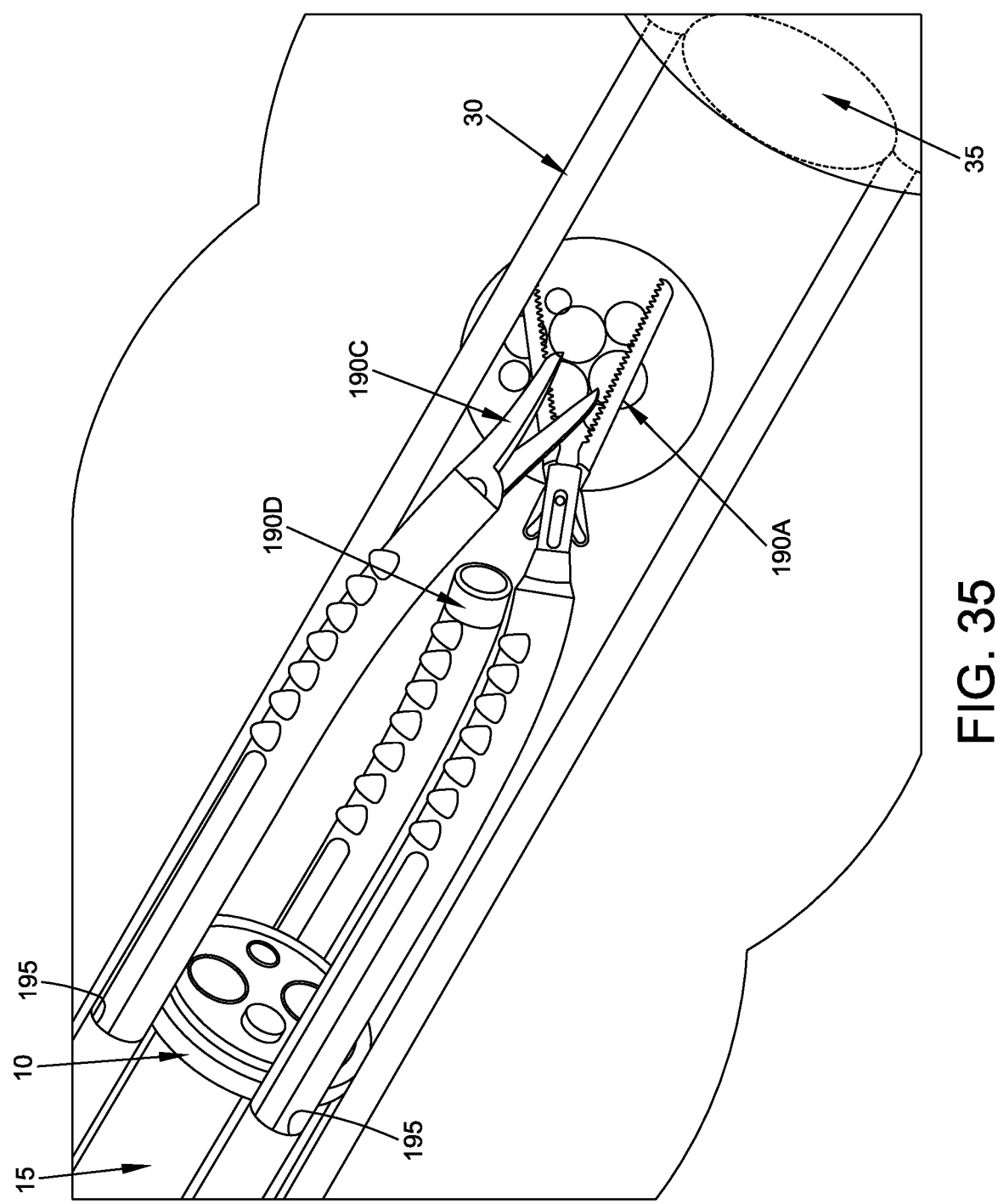

More particularly, and looking now at FIG. 31, there is shown an end view of another form of sleeve 15 which includes a plurality of lumens 195 for slidably receiving instruments 190 therein. Note that, when inflated, aft balloon 20 provides a secure platform for maintaining endoscope 10 and sleeve 15 within a body lumen or body cavity, with endoscope 10 and sleeve 15 centered within the body lumen or body cavity. As a result, the distal ends of lumens 195 of sleeve 15 will also be securely maintained within the body lumen or body cavity so as to provide a secure support for instruments advanced through lumens 195 of sleeve 15.

The proximal ends of lumens 195 may extend to, and through, base 25, in which case instruments may be inserted into lumens 195 at base 25, or the proximal ends of lumens 195 may terminate proximal to base 25 (but still outside the body of the patient), in which case instruments may be inserted into lumens 195 intermediate sleeve 15. By way of example but not limitation, where endoscope 10 is 180 cm in length and instruments 190 are 60 cm in length, it can be advantageous to insert instruments 190 into lumens 195 at a point closer to balloons 20, 35 (rather than at base 25). Note that in FIG. 31, the lumen 47 for receiving inflation/deflation tube 45 and inflation/deflation tube 45 for inflating/deflating aft balloon 20 are not visible, since the view is distal-facing and is taken at a location distal to where lumen 47 and inflation/deflation tube 45 terminate on sleeve 15.

FIGS. 32-35 show various instruments 190 extending out of lumens 195. Note that instruments 190 preferably comprise articulating instruments, e.g., graspers 190A in FIGS. 32-35, a cauterizing device 190B in FIGS. 32-33, scissors 190C in FIGS. 34 and 35, and a suction device 190D in FIGS. 32-35.

It should be appreciated that where sleeve 15 comprises its central passageway for receiving endoscope 10, lumen 47 for receiving inflation/deflation tube 45, lumens 52 for receiving support tubes 50 which receive push tubes 30, and/or lumens 195 for slidably receiving instruments 190 therein, sleeve 15 is preferably formed by an extrusion process.

In one preferred form of the invention, lumen 47 for receiving inflation/deflation tube 45, lumens 52 for receiving support tubes 50 which receive push tubes 30, and/or lumens 195 for slidably receiving instruments 190 may have a fixed configuration (i.e., a fixed diameter), so that sleeve 15 has a fixed outer profile.

In another preferred form of the invention, lumen 47 for receiving inflation/deflation tube 45, lumens 52 for receiving support tubes 50 which receive push tubes 30, and/or lumens 195 for slidably receiving instruments 190 may have an expandable configuration (i.e., they may have a minimal profile when empty and expand diametrically as needed when filled), so that the overall profile of sleeve 15 is minimized.

It should also be appreciated that where sleeve 15 comprises a plurality of lumens 195 for slidably receiving instruments 190 therein, it can be desirable to provide greater structural integrity to the distal ends of lumens 195 so as to provide improved support for the instruments 190 received within lumens 195. To this end, a support ring may be provided at the distal end of sleeve 15, wherein the support ring provides openings for the passage of push tubes 30 and openings for the passage of instruments 190. Note that the openings in such a support ring for the passage of instruments 190 preferably make a close fit with the instruments so as to provide excellent instrument support at the distal end of sleeve 15.

Alternatively and/or additionally, lumens 195 may accommodate hollow instrument guide tubes which themselves accommodate instruments therein. Such hollow instrument guide tubes can provide greater structural integrity to the distal ends of lumens 195 so as to provide improved support for the instruments 190 received within lumens 195. And such hollow instrument guide tubes may be of fixed geometry or of bendable or articulating geometry. See, for example, FIG. 36, which shows hollow instrument guide tubes 200 extending out of lumens 195 and receiving instruments 190 therein. Note that hollow instrument guide tubes 200 may be independently movable relative to one another (and independently movable relative to sleeve 15). Note also that instruments 190 preferably make a close fit with hollow instrument guide tubes 200 so as to provide excellent instrument support at the distal end of sleeve 15.

It should also be appreciated that, if desired, the two push tubes 30 may be replaced by a single push tube 30 or by more than two push tubes 30, e.g., by three push tubes 30. It will be appreciated that, where a plurality of push tubes 30 are provided, it will generally be desirable to equally-circumferentially-space the push tubes from one another, e.g., where two push tubes 30 are provided, it is generally desirable that the two push tubes 30 be spaced 180 degrees apart, where three push tubes 30 are provided, it is generally desirable that the push tubes be spaced 120 degrees apart, etc.

Applications

Thus it will be seen that the present invention comprises the provision and use of novel apparatus for manipulating the side wall of a body lumen and/or body cavity so as to better present the side wall tissue (including visualization of areas initially hidden or outside the field of view) for examination and/or treatment during an endoscopic procedure, e.g., to straighten bends, "iron out" inner luminal surface folds and create a substantially static or stable side wall of the body lumen and/or body cavity which enables more precise visual examination (including visualization of areas initially hidden or outside the field of view) and/or therapeutic intervention. By way of example but not limitation, the novel apparatus can be used to stabilize, straighten, expand and/or flatten bends and/or curves and/or folds in the side wall of the intestine so as to better present the side wall tissue (including visualization of areas initially hidden or outside the field of view) for examination and/or treatment during an endoscopic procedure.

The present invention also comprises the provision and use of novel apparatus capable of steadying and/or stabilizing the distal tips and/or working ends of instruments (e.g., endoscopes, articulating and/or non-articulating devices such as graspers, cutters or dissectors, cauterizing tools, ultrasound probes, etc.) inserted into a body lumen and/or body cavity during an endoscopic procedure with respect to the side wall of the body lumen and/or body cavity, whereby to facilitate the precision use of those instruments.

By way of example but not limitation, the present apparatus can provide a stable platform (i.e., a stable endoscope, stable therapeutic tools and a stable colon wall, all stable with respect to one another) for the performance of numerous minimally-invasive procedures within a body lumen and/or body cavity, including the stabilization of an endoscope and/or other surgical instruments (e.g., graspers, cutters or dissectors, cauterizing tools, ultrasound probes, etc.) within the body lumen and/or body cavity, e.g., during a lesion biopsy and/or lesion removal procedure, an organ resection procedure, endoscopic submucosal dissection (ESD), endoscopic mucosal resection (EMR), etc., while at the same time stabilizing the colon (including decreasing deformation of the colon wall) so as to enable more precise visualization, intervention and/or surgery.

Significantly, the present invention provides novel apparatus capable of steadying and/or stabilizing the distal tips and/or working ends of endoscopes (and hence also steadying and/or stabilizing the distal tips and/or working ends of other instruments inserted through the working channels of those endoscopes, such as graspers, cutters or dissectors, cauterizing tools, ultrasound probes, etc.) with respect to the side wall of the body lumen and/or body cavity, and stabilizing the side wall of the body lumen and/or body cavity relative to these instruments.

And the present invention provides novel apparatus capable of steadying and/or stabilizing the distal tips and/or working ends of instruments (such as graspers, cutters or dissectors, cauterizing tools, ultrasound probes, etc.) advanced to the surgical site by means other than through the working channels of endoscopes.

The novel apparatus of the present invention can be used in substantially any endoscopic procedure to facilitate the alignment and presentation of tissue during an endoscopic procedure and/or to stabilize the working end of an endoscope (and/or other instruments advanced through the endoscope) relative to tissue or to assist in the advancement of the endoscope during such a procedure.

The present invention is believed to have widest applications with respect to the gastrointestinal (GI) tract (e.g., large and small intestines, esophagus, stomach, etc.), which is generally characterized by frequent turns and which has a side wall characterized by numerous folds and disease processes located on and between these folds. However, the methods and apparatus of the present invention may also be used inside other body lumens (e.g., blood vessels, lymphatic vessels, the urinary tract, fallopian tubes, bronchi, bile ducts, etc.) and/or inside other body cavities (e.g., the head, chest, abdomen, nasal sinuses, bladder, cavities within organs, etc.).

Modifications

While the present invention has been described in terms of certain exemplary preferred embodiments, it will be readily understood and appreciated by those skilled in the art that it is not so limited, and that many additions, deletions and modifications may be made to the preferred embodiments discussed above while remaining within the scope of the present invention.

What is claimed is:

1. Apparatus comprising:
   a sleeve having a distal end, a proximal end, and a central lumen extending therebetween, the central lumen being sized to receive an endoscope therein, wherein the endoscope comprises a distal end and a proximal end, wherein the proximal end of the endoscope comprises a handle, wherein the sleeve is sized to extend over the endoscope from a location adjacent to the distal end of the endoscope to a location adjacent to the handle of the endoscope, and further wherein the sleeve comprises a push tube channel having a distal end and a proximal end, wherein the distal end of the push tube channel is disposed adjacent to the distal end of the sleeve and the proximal end of the push tube channel is disposed adjacent to the proximal end of the sleeve;
   a proximal balloon secured to said sleeve;
   an inflation/deflation tube carried by said sleeve and in fluid communication with the interior of said proximal balloon;
   a push tube slidably disposed in the push tube channel of said sleeve so as to be movable relative to said sleeve, wherein the push tube comprises a distal end and a proximal end, with the distal end of the push tube being configured to extend out of the distal end of the push tube channel, and with the proximal end of the push tube being configured to extend out the proximal end of the push tube channel; and
   a distal balloon secured to the distal end of said push tube, the interior of said distal balloon being in fluid communication with said push tube, wherein said distal balloon is capable of assuming a deflated condition and an inflated condition; and
   at least one tool lumen carried by the sleeve, wherein said at least one tool lumen opens at said distal end of said sleeve, distal to said proximal balloon and proximal to said distal balloon, whereby to facilitate advancement of a tool to said distal end of said sleeve such that said tool exits said sleeve in the space between said proximal balloon and said distal balloon.

2. Apparatus according to claim 1 wherein said at least one tool lumen extends between a proximal opening and a distal opening, and wherein the distal opening of said at least one tool lumen opens at said distal end of said sleeve, distal to said proximal balloon and proximal to said distal balloon.

3. Apparatus according to claim 2 wherein said proximal opening of said tool lumen opens at said proximal end of said sleeve.

4. Apparatus according to claim 2 wherein said proximal opening of said tool lumen opens intermediate said proximal end of said sleeve and said distal end of said sleeve.

5. Apparatus according to claim 1 further comprising at least two tool lumens carried by said sleeve.

6. Apparatus according to claim 1 wherein a tool is disposed in said at least one tool lumen such that the tool can be deployed from said at least one tool lumen into the space distal to said proximal balloon and proximal to said distal balloon.

7. Apparatus according to claim 6 wherein said tool comprises one selected from the group consisting of a grasper, a cutter or dissector, a cauterizing tool, and an ultrasound probe.

8. Apparatus according to claim 1 wherein said at least one tool lumen is radially expandable such that said at least one tool lumen comprises a radially-reduced profile when said at least one tool lumen is empty and a radially-expanded profile when said at least one tool lumen has a tool disposed therein.

9. Apparatus according to claim 2 wherein said at least one tool lumen comprises a support ring mounted to the distal opening of said at least one tool lumen.

10. Apparatus according to claim 1 wherein said at least one tool lumen further comprises a hollow instrument guide tube disposed therein for providing support to tools disposed within said at least one tool lumen.

11. Apparatus according to claim 10 wherein said hollow instrument guide tube comprises a fixed geometry.

12. Apparatus according to claim 10 wherein said hollow instrument guide tube is bendable.

13. Apparatus according to claim 10 wherein said hollow instrument guide tube is articulatable.

* * * * *